(12) United States Patent
Collonges et al.

(10) Patent No.: US 6,509,499 B1
(45) Date of Patent: Jan. 21, 2003

(54) NITROMETHYLTHIOBENZENE DERIVATIVES AS INHIBITORS OF ALDOSE REDUCTASE

(75) Inventors: François Collonges, Beynost (FR); Hervé Dumas, Vaulx-Milieu (FR); Claude Lardy, Lyons (FR); Philippe Durbin, Villeurbanne (FR)

(73) Assignee: Merck PatentGesellschaft mit, Darmstadt (DE)

( * ) Notice: Subject to any disclaimer, the term of this patent is extended or adjusted under 35 U.S.C. 154(b) by 0 days.

(21) Appl. No.: 09/331,662

(22) PCT Filed: Dec. 12, 1997

(86) PCT No.: PCT/EP97/06981

§ 371 (c)(1),
(2), (4) Date: Mar. 17, 2000

(87) PCT Pub. No.: WO98/28265

PCT Pub. Date: Jul. 2, 1998

(30) Foreign Application Priority Data

Dec. 23, 1996 (FR) .............................................. 96 15887

(51) Int. Cl.⁷ ........................ C07C 311/03; A61K 31/18
(52) U.S. Cl. ........................ 564/90; 514/445; 514/468; 514/604; 514/605; 549/44; 549/48; 549/65; 564/92; 564/99
(58) Field of Search .............................. 564/90, 92, 99; 514/604, 468, 445, 605; 549/44, 48, 65

(56) References Cited

U.S. PATENT DOCUMENTS

| | | | |
|---|---|---|---|
| 5,110,808 A | 5/1992 | Brittain et al. | |
| 5,153,227 A | 10/1992 | Brown et al. | |
| 5,250,570 A | 10/1993 | Brittain et al. | |
| 5,430,060 A | 7/1995 | Brittain et al. | |

FOREIGN PATENT DOCUMENTS

| | | |
|---|---|---|
| CA | 2026003 | 8/1990 |
| CA | 2048345 | 2/1992 |
| EP | 0304190 | 2/1989 |
| EP | 0469887 | 2/1992 |
| EP | 0469888 | 2/1992 |
| EP | 0469889 | 2/1992 |
| WO | 9008761 | 4/1990 |

*Primary Examiner*—Shailendra Kumar
(74) *Attorney, Agent, or Firm*—Millen, White, Zelano & Branigan, P.C.

(57) ABSTRACT

The invention concerns novel compound of general formula (1) in which: P, $T_1$, $T_2$, X and n are as defined in claim 1, their tautomeric forms, and their additive salts with pharmaceutically acceptable bases. The invention also concerns methods for preparing these compounds and their applications as medicines. These compounds inhibit the aldose reductase enzyme and can be used in the treatment or prevention of peripheral and autonomous neurological diabetic complications, renal and ocular disorders such as cataract and retinopathy.

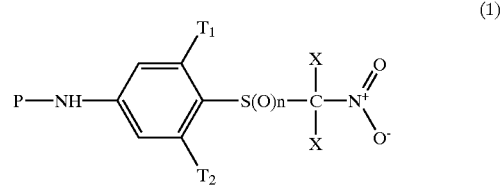

(1)

28 Claims, No Drawings

NITROMETHYLTHIOBENZENE DERIVATIVES AS INHIBITORS OF ALDOSE REDUCTASE

This application is a 371 of PCT/EP97/06981, filed Dec. 12, 1997.

The present invention relates to novel nitromethylthiobenzene derivatives, the processes for preparing them and to their therapeutic application, more particularly in the treatment or prevention of diabetic complications.

Diabetes is characterized by a high concentration of glucose in the blood. This glucose is normally metabolized by the enzyme hexokinase during the first step of glycolysis, resulting in degradation to pyruvate. When the glucose concentration is too high, the hexokinase becomes saturated, and a second glucose metabolization route comes into play; this is the polyol route which successively involves two enzymes: aldose reductase which converts the glucose into sorbitol, and sorbitol dehydrogenase which converts the sorbitol into fructose. In the case of diabetes, the excess glucose accelerates the formation of sorbitol, which tends to accumulate. This results in serious metabolic disturbances, such as, for example, an increase in osmotic pressure, which is liable to lead to tissue degeneration. Aldose reductase inhibitors are thus useful for treating or preventing some of the complications induced by diabetes.

Many products are described in the literature as being aldose reductase inhibitors which are active in vitro and in vivo. They are mainly hydantoin derivatives, succinimides and acetic acids. More recently, (phenylsulphonyl)nitromethane derivatives have appeared in European patent 304,190, and in particular the compound 3,5-dimethyl-4-[(nitromethyl)sulphonyl]aniline in patent WO 90/08761. This compound has generated several derived series, such as the N-acylation products described in European patent 469,887 and the (oxamido- and ureido-phenylsulphonyl) hitromethanes described in European patent 469,889.

The present invention relates to nitromethylthiobenzene derivatives corresponding to the general formula 1,

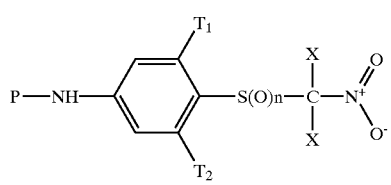

(1)

in which:

P represents the radical (i): $-(CO-NH)_m-SO_2-R$;

the radical (ii):

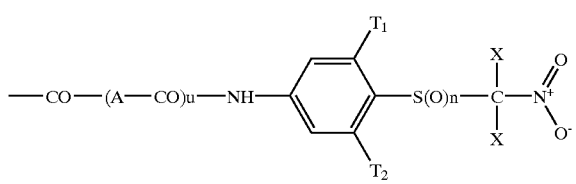

or the radical (iii):

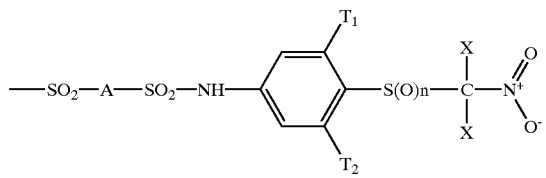

R represents a radical chosen from phenyl, benzyl, diphenylmethyl, naphthyl, cycloalkylalkyl in which the alkyl part is $C_1-C_4$ and the cycloalkyl part is $C_3-C_7$, and styryl, the said radical optionally being substituted with one or more groups Z which may be identical or different, or alternatively R represents a $C_3-C_5$ aromatic heterocyclic radical comprising 1 or 2 hetero atoms chosen from O, S and N, the said radical optionally being substituted with one or more groups Z, which may be identical or different, and optionally being fused to 1 or 2 phenyl rings which are optionally substituted with one or more groups Z, which may be identical or different; or alternatively R represents $C_1-C_4$ alkyl optionally substituted with one or more halogen atoms, which may be identical or different, $C_3-C_7$ cycloalkyl or cyclo($C_3-C_7$)alkyl ($C_1-C_4$)alkyl;

Z is chosen from a halogen atom, a $C_1-C_4$ alkyl, $C_1-C_4$ alkoxy, nitro, cyano, trifluoromethyl, trifluoromethoxy, ($C_2-C_5$)alkylamino, ($C_1-C_4$)alkylsulphonyl, ($C_1-C_4$)alkylthio and phenyl group;

X represents a hydrogen or halogen atom;

m is 0 or 1;

n is 0, 1 or 2;

$T_1$ and $T_2$ represent, independently of each other, a hydrogen atom or a $C_1-C_4$ alkyl group, u is 0 or 1;

A represents $C_1-C_8$ alkylene or the group

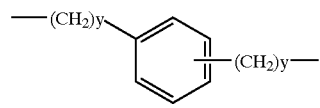

y being an integer chosen from 0, 1, 2, 3 and 4; it being understood that when P represents the radical (ii), A can also represent a bond;

the tautomeric forms thereof and the addition salts thereof with pharmaceutically acceptable bases.

The term "$C_1-C_4$ alkyl" denotes a linear or branched saturated hydrocarbon-based radical comprising from 1 to 4 carbon atoms. The alkoxy group consequently denotes the group alkyl-O— in which alkyl has the meaning indicated above.

As $C_3-C_5$ aromatic heterocycles comprising 1 or 2 hetero atoms chosen from O, S and N, mention may be made of furan, thiophene, pyrrole, oxazole, thiazole, imidazole, pyrazole, isoxazole, isothiazole, pyridine, pyridazine, pyrimidine and pyrazine, pyridine and thiophene being preferred.

As it is used herein, term "halogen" denotes a fluorine, bromine, chlorine or iodine atom.

Examples of cycloalkyl groups are cyclopropyl, cyclobutyl, cyclopentyl and cyclohexyl groups. According to the invention, the cycloalkyalkyl group denotes an alkyl group substituted with a cycloalkyl group.

The term "alkylene radical" refers to a linear or branched divalent hydrocarbon-based saturated chain such as —CH$_2$—; —CH$_2$—CH$_2$—CH$_2$—; or —CH$_2$—CH(CH$_3$)—CH$_2$—.

The group of formula:

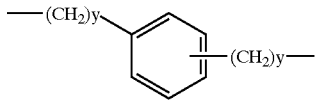

corresponds to one of the following formulae:

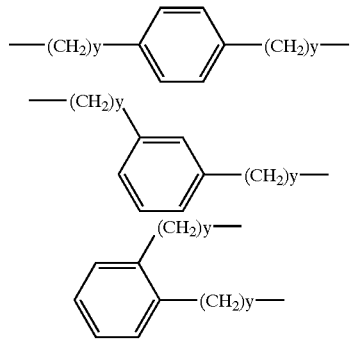

in which y represents 0, 1, 2, 3 or 4.

According to the invention, when P represents the radical (ii) of formula:

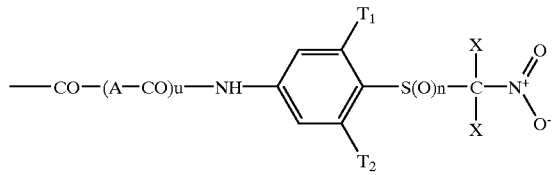

A is chosen from:
  a bond, a C$_1$–C$_8$ alkylene radical, and
  the group of formula

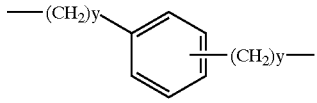

in which y is an integer chosen from 0, 1, 2, 3 and 4.

Conversely, when P is —(CO—NH)$_m$—SO$_2$—R or the radical (iii) of formula:

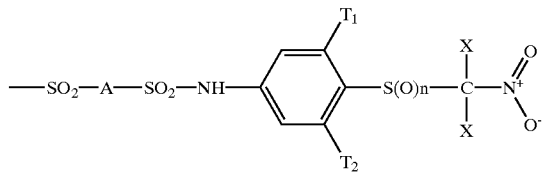

then A is chosen from:
  a C$_1$–C$_8$ alkylene radical, and
  the group of formula:

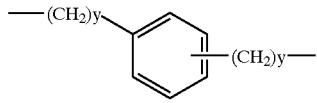

in which y is an integer chosen from 0, 1, 2, 3 and 4.

The possible tautomeric forms of the compounds of formula 1 form an integral part of the invention.

The addition salts, with pharmaceutically acceptable bases, of compounds of formula 1 in which X is a hydrogen atom and n is equal to 1 or 2 also form an integral part of the invention, for example an alkali or alkaline-earth metal salt, such as a sodium, potassium, calcium or magnesium salt, an aluminium salt, an ammonium salt or a salt of an organic base bearing a pharmaceutically acceptable cation.

A first group of preferred compounds consists of the compounds of formula 1 in which:
  P represents —(CO—NH)$_m$—SO$_2$—R
  R represents a radical chosen from phenyl, diphenylmethyl, naphthyl and styryl, the said radical optionally being substituted with one or more groups Z, which may be identical or different, or alternatively
  R represents a C$_3$–C$_5$ aromatic heterocyclic radical comprising 1 or 2 hetero atoms chosen from O, S and N, the said radical optionally being substituted with one or more groups Z, which may be identical or different, and optionally being fused to 1 or 2 phenyl rings which are optionally substituted with one or more groups Z, which may be identical or different; or alternatively
  R represents C$_1$–C$_4$ alkyl optionally substituted with one or more halogen atoms, which may be identical or different, C$_3$–C$_7$ cycloalkyl or cyclo(C$_3$–C$_7$)alkyl (C$_1$–C$_4$)-alkyl;
  Z, X, m and n being as defined above for formula (1).

A second group of preferred compounds includes the compounds of formula 1 in which:
  P represents —(CO—NH)$_m$—SO$_2$—R,
  R represents phenyl; phenyl substituted with one or more groups Z, which may be identical or different; benzyl; benzyl substituted with one or more groups Z which may be identical or different; C$_1$–C$_4$ alkyl optionally substituted with one or more halogen atoms, which may be identical or different; C$_3$–C$_7$ cycloalkyl; cyclo(C$_3$–C$_7$)alkyl(C$_1$–C$_4$)alkyl; styryl; thienyl; pyridyl; naphthyl; dibenzofuryl; or diphenylmethyl;
  Z is chosen from a halogen atom, a C$_1$–C$_4$ alkyl, C$_1$–C$_4$ alkoxy, nitro, trifluoromethyl, trifluoromethoxy, (C$_2$–C$_5$)alkylamino, (C$_1$–C$_4$)alkylsulphonyl and phenyl group;
  X, m and n being as defined above for formula (1).

Among this second group of preferred compounds, the compounds for which:
  P represents —(CO—NH)$_m$—SO$_2$—R,
  R represents phenyl; phenyl substituted with one or more groups Z, which may be identical or different; benzyl; benzyl substituted with one or more groups Z which may be identical or different; methyl; C$_3$–C$_7$ cycloalkyl; cyclo(C$_3$–C$_7$)alkyl(C$_1$–C$_4$)alkyl; styryl; thienyl; pyridyl; naphthyl; dibenzofuryl; diphenylmethyl or 2,2,2-trifluoroethyl;
  Z is chosen from fluoro, chloro, bromo, methyl, methoxy, nitro, trifluoromethyl, trifluoromethoxy, acetamido, methylsulphonyl and phenyl;

X represents hydrogen or chlorine;

m and n being as defined above for formula (1), are particularly advantageous.

A third group of preferred compounds consists of the compounds of formula 1 in which:

P represents —(CO—NH)$_m$—SO$_2$—R,

R represents phenyl; phenyl substituted with one or more groups Z, which may be identical or different; methyl; C$_3$–C$_7$ cycloalkyl; cyclo(C$_3$–C$_7$)alkyl(C$_1$–C$_4$)alkyl; styryl; thienyl; pyridyl; naphthyl; dibenzofuryl; diphenylmethyl or 2,2,2-trifluoroethyl;

Z is chosen from fluoro, chloro, bromo, methyl, methoxy, nitro, trifluoromethyl, trifluoromethoxy, acetamido, methylsulphonyl and phenyl;

X represents hydrogen or chlorine;

m and n being as defined above for formula (1).

A fourth group of preferred compounds consists of the compounds of formula (1) in which:

P represents:

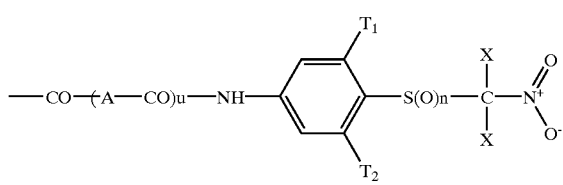

A represents a bond or C$_1$–C$_8$ alkylene, u, n, X, T$_1$ and T$_2$ being as defined above for formula (1).

A fifth group of preferred compounds consists of the compounds of formula (1) in which:

P represents:

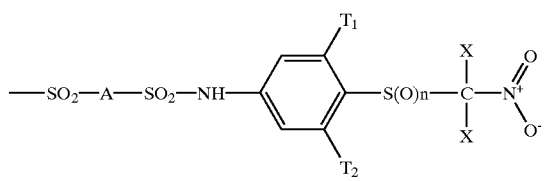

A represents the group

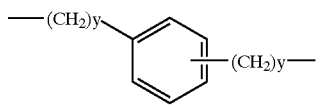

n, X, y, T$_1$ and T$_2$ being as defined above for formula (1).

Compounds which are particularly preferred are the following:

N-[3,5-dimethyl-4-[(nitromethyl)sulphonyl]phenyl]benzenesulphonamide;

3,4-difluoro-N-[3,5-dimethyl-4-[(nitromethyl)sulphonyl]phenyl]benzenesulphonamide;

3-bromo-N-[3,5-dimethyl-4-[(nitromethyl)sulphonyl]phenyl]benzenesulphonamide;

N-[3,5-dimethyl-4-[(nitromethyl)sulphonyl]phenyl]-2-(trifluoromethyl)benzenesulphonamide;

N-[3,5-dimethyl-4-[(nitromethyl)sulphonyl]phenyl]-4-fluorobenzenesulphonamide;

N-[3,5-dimethyl-4-[(nitromethyl)sulphonyl]phenyl]-3-fluorobenzenesulphonamide;

N-[3,5-dimethyl-4-[(nitromethyl)sulphonyl]phenyl]phenylmethanesulphonamide; 2,3-difluoro-N-[3,5-dimethyl-4-[(nitromethyl)sulphonyl]phenyl]benzenesulphonamide; 3,5-difluoro-N-[3,5-dimethyl-4-[(nitromethyl)sulphonyl]phenyl]benzenesulphonamide;

N-[3,5-dimethyl-4-[(nitromethyl)sulphonyl]phenyl]-2-fluorobenzenesulphonamide, and the following compounds:

N,N'-bis[3,5-dimethyl-4-[(nitromethyl)sulphonyl]phenyl]-1,5-pentanediamide;

N,N'-bis[3,5-dimethyl-4-[(nitromethyl)sulphonyl]phenyl]-1,8-octanediamide;

N,N'-bis[4-[(nitromethyl)sulphonyl]phenyl]-1,5-pentanediamide;

N,N'-bis[3,5-dimethyl-4-[(nitromethyl)sulphonyl]phenyl]-ethanediamide;

N,N'-bis[3,5-dimethyl-4-[(nitromethyl)sulphonyl]phenyl]-urea;

N,N'-bis[3,5-dimethyl-4-[(nitromethyl)sulphonyl]phenyl]-1,4-butanediamide;

N,N'-bis[3,5-dimethyl-4-[(nitromethyl)sulphonyl]phenyl]-1,3-propanediamide;

N,N'-bis[3,5-dimethyl-4-[(nitromethyl)sulphonyl]phenyl]-1,3-benzenedisulphonamide;

N,N'-bis[3,5-dimethyl-4-[(nitromethyl)sulphonyl]phenyl]-1,3-benzenedimethane sulphonamide.

The compounds of the invention are prepared according to the following methods:

(A) When P represents —(CO—NH)$_m$—SO$_2$—R, X is a hydrogen atom, m is equal to 0 and n is equal to 2, a sulphonyl chloride of formula RSO$_2$Cl, R having the meanings defined above, is reacted with the compound of formula 2,

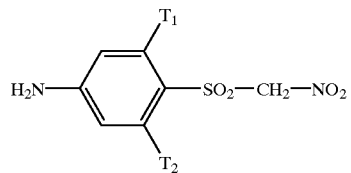

in which T$_1$ and T$_2$ are as defined above for (1), in the presence of a suitable base.

The reaction is preferably carried out in a solvent, for example a polar aprotic solvent such as tetrahydrofuran at a temperature between 10° C. and the boiling point of the solvent.

As bases which are particularly suitable, mention may be made of calcium carbonate (method A1) or pyridine (method A2).

(B) When P represents —(CO—NH)$_m$—SO$_2$—R, X is a halogen atom, preferably chlorine, m is equal to 0 and n is equal to 2, the appropriate N-halosuccinimide is reacted with a compound of the formula 3

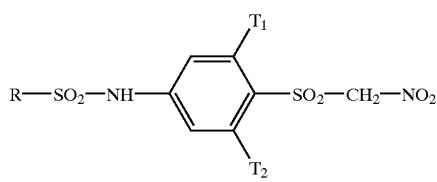

in which R, T$_1$ and T$_2$ have the meanings defined above for (1), in the presence of a free-radical generator such as 2,2'-azobisisobutyronitrile.

The reaction is preferably carried out in a solvent, for example a halohydrocarbon such as carbon tetrachloride, maintained at reflux.

(C) When P represents —(CO—NH)$_m$—SO$_2$—R, X is a hydrogen atom, m is equal to 1 and n is equal 2, a sulphonyl isocyanate of formula R—SO$_2$—N=C=O, R having the meanings defined above, is reacted with the compound of formula 2 defined above.

The reaction is preferably carried out in a solvent, for example a halohydrocarbon such as methylene chloride, at a temperature in the region of room temperature.

(D) When P represents —(CO—NH)$_m$—SO$_2$—R, X is a hydrogen atom and m and n are equal to 0, a sulphonyl chloride of formula RSO$_2$Cl, R having the meanings defined above, is reacted with the compound of formula 10,

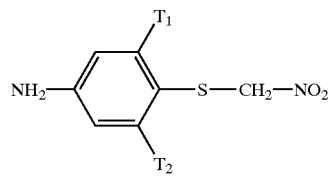

in which T$_1$ and T$_2$ are as defined for (1), in the presence of a suitable base.

The reaction is preferably carried out in a solvent, for example a polar aprotic solvent such as tetrahydrofuran, at a temperature in the region of room temperature. A particularly suitable base is, for example, calcium carbonate.

(E) When P represents —(CO—NH)$_m$—SO$_2$—R, X is a hydrogen atom, m is equal to 0 and n is equal to 1, an oxidizing agent such as m-chloroperbenzoic acid is reacted with a compound of formula 4,

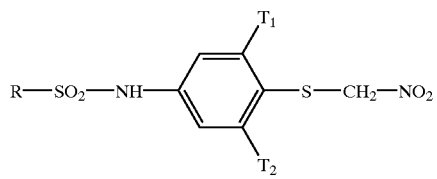

in which R, T$_1$ and T$_2$ have the meanings defined above.

The process is preferably performed in a solvent, for example chloroform, at a temperature in the region of room temperature.

(F) When P represents the radical (ii) of formula:

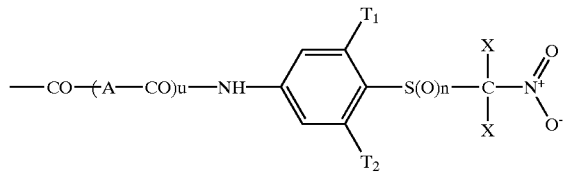

u is 1, X represents a hydrogen atom and n is equal to 2, the dichloride of formula 5 below:

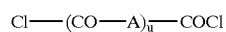

is reacted with at least two molar equivalents of compound of formula 2 defined above, in the presence of a base.

The reaction is preferably carried out in a solvent, for example a polar aprotic solvent such as tetrahydrofuran, at a temperature of between 10° C. and the boiling point of the solvent.

As bases which are particularly suitable, mention may be made of calcium carbonate (method F1) or pyridine (method F2).

The molar ratio of the compound of formula 2 to the compound of formula 5 is preferably between 2 and 4. However, it should be understood that a larger amount of aniline derivative can be used without any adverse effect.

(G) When P represents the radical (iii) of formula:

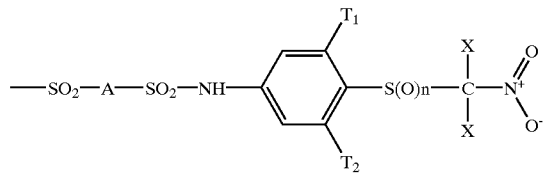

X represents a hydrogen atom and n is equal to 2, the sulphonyl dichloride of formula 6 below:

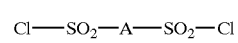

is reacted with at least two molar equivalents of compound of formula 2 defined above, in the presence of a base.

Here also, calcium carbonate (method G1) and pyridine (method G2) constitute preferred examples of suitable bases.

The reaction is advantageously carried out in a polar aprotic solvent at between 10° C. and the boiling point of the solvent.

It generally suffices to react 2 to 4 molar equivalents of compound of formula 2 with dichloride of formula 6, although a larger amount does not harm the reaction.

(H) When P represents the radical (ii) of formula:

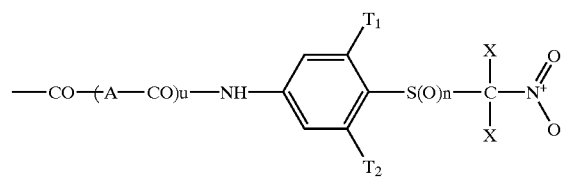

in which u is zero, X represents a hydrogen atom and n is equal to 2, trichloromethyl chloroformate is reacted with at least two molar equivalents of compound of formula 2 defined above in the presence of base.

The reaction is preferably carried out in a polar aprotic solvent such as tetrahydrofuran, at a temperature of between 10° C. and the boiling point of the solvent.

As a base which is particularly suitable, mention may be made of calcium carbonate. The molar ratio of the compound of formula 2 to the trichloromethyl chloroformate is preferably between 2 and 4.

The intermediate compound of formula 2 defined above is obtained as described in patent WO 90/08761 by basic hydrolysis of the compound of formula 9. The latter compound was prepared according to the following method, in particular using the novel reaction of nitromethanesodium with the aryl thiocyanate 7 to give the compound 8:

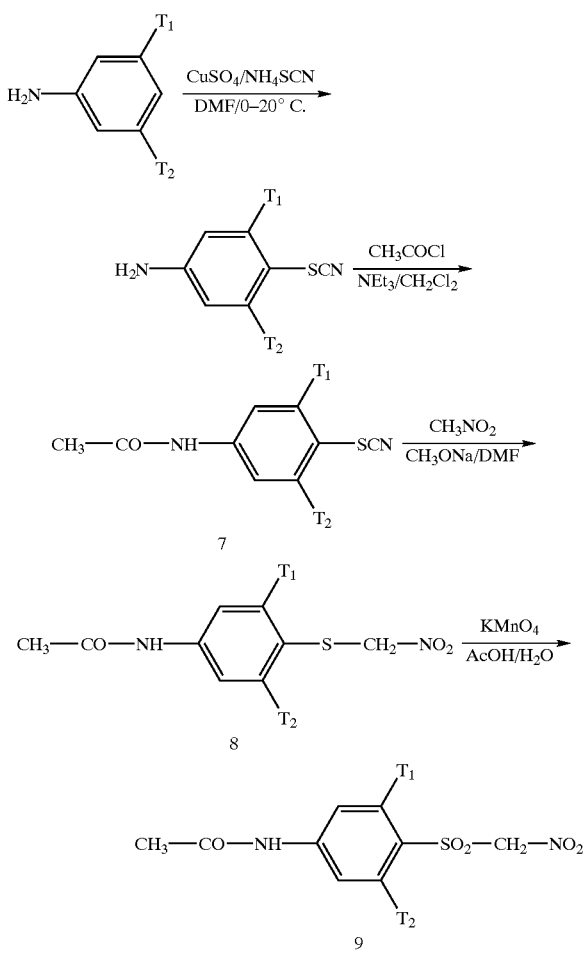

The intermediate compound of formula 10 is obtained by basic hydrolysis of the compound of formula 8.

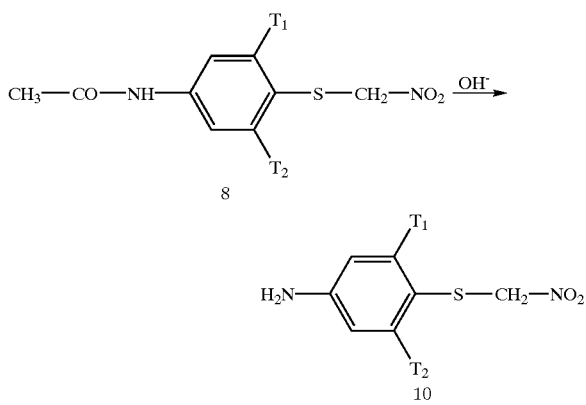

One specific embodiment of this process consists in preparing 3,5-dimethyl-4-[(nitromethyl)sulphonyl]aniline, which corresponds to the compound of formula 2 in which $T_1$ and $T_2$ represent —$CH_3$.

The inhibition of the enzyme aldose reductase and the reduction of the accumulation of sorbitol can be demonstrated in standardized laboratory tests below:

1) In Vitro Study: Inhibition of Aldose Reductase

The aldose reductase used is obtained from the lenses of male Wistar rats according to a modification of the method by S. Hayman et al. (Journal of Biological Chemistry 240, p. 877, 1965). The enzymatic extract is diluted in a phosphate buffer in the presence of NADPH and various concentrations of the test products. The reaction is triggered with L-glyceraldehyde and the rate of reaction is measured by monitoring the disappearance of the NADPH by spectrophotometry at 340 nm. The rate of reaction is calculated for each concentration of products, and the concentration required for a 50% reduction in the rate of reaction ($IC_{50}$) is then evaluated by linear interpolation.

2) In Vivo Study: Reduction of the Accumulation of Sorbitol

Male Wistar rats weighing from 200 to 250 g are made diabetic by intravenous injection of streptozotocin (60 mg/kg). They then receive an oral treatment of the test products, in the form of a suspension, 4 hours, 30 hours and 52 hours after the injection of streptozotocin. 18 hours after the final oral treatment, the rats are sacrificed and decapitated and their sciatic nerves are then removed. After extraction, the level of sorbitol in the nerves is measured according to the enzymatic method described by H. J. Bergmeyer (Methods of enzymatic analysis, H. U. Bergmeyer ed., Academic Press New York 3, p. 1323, 1974). The percentage of protection is calculated for each product relative to the batch of diabetic animals, taking into account the level of sorbitol in the sciatic nerves of non-diabetic rats.

By way of example, the results obtained for some of the test products are given in the table below:

| Products Example No. | Inhibition of aldose reductase in vitro $IC_{50}$ (nM) | Protection against the increase in sorbitol (%) (5 mg/kg/day p.o.) |
| --- | --- | --- |
| 1 | 8 | 65 |
| 10 | 7 | 66 |
| 13 | 8 | 70 |
| 14 | 7 | 70 |
| 24 | 8 | 80 |
| 25 | 7 | 85 |
| 26 | 6 | 104 |
| 29 | 7 | 71 |
| 30 | 8 | 87 |
| 34 | 9 | 69 |

The compounds of the invention can be used as medicinal products as aldose reductase inhibitors, and in particular in the treatment of diabetic complications such as cataracts, retinopathies, neuropathies, nephropathies and certain vascular diseases.

These medicinal products can be administered orally in the form of immediate-release or controlled-release tablets, gelatin capsules or granules, intravenously in the form of an injectable solution, transdermally in the form of an adhesive transdermal device, or topically in the form of eyedrops, a solution, cream or gel.

The active principle is combined with various pharmaceutical excipients. The daily doses can range from 5 mg to 200 mg of active principle.

A number of pharmaceutical formulations are given below as non-limiting examples:

Composition of an immediate-release tablet

Active principle     100 mg
Excipients: lactose, wheat starch,

| | |
|---|---|
| polyvidone, talc, magnesium stearate Composition of a controlled-release tablet | |
| Active principle | 100 mg |
| Excipients: lactose, polyvidone, talc, magnesium stearate, polymer (cellulose derivative or acrylic and methacrylic derivative or vinyl or glyceride derivative) Composition of a gelatin capsule | |
| Active principle | 100 mg |
| Excipients: lactose, wheat starch, talc, magnesium stearate Composition of a vial of injectable solution | |
| Active principle | 200 mg |
| Excipients: mannitol, water for injectable preparation Composition of a cream (composition for 100 g of cream) | |
| Active principle | 2 g |
| Excipients: self-emulsifying cetylstearyl alcohol, cetylaryl octanoate, nipasol, sorbic acid, propylene glycol, carbopol Composition of an eyedrop | |
| Active principle | 15 mg |
| Excipients: sodium chloride, benzalkonium chloride, water for injectable preparation. | |

The examples which follow illustrate the invention in a non-limiting manner.

The following abbreviations have been used in the nuclear magnetic resonance (NMR) data: s for singlet, d for doublet, t for triplet, q for quartet and m for complex multiplet; the chemical shifts δ are expressed in ppm.

EXAMPLE 1

(Method A1)

N-[3,5-Dimethyl-4-[(nitromethyl)sulphonyl]phenyl-benzenesulphonamide 7.85 g (78.4 mmol) of calcium carbonate and 7.45 ml (58.4 mmol) of benzenesulphonyl chloride are successively added to a mixture, maintained under a nitrogen atmosphere, of 9.5 g (38.9 mmol) of 3,5-dimethyl-4-[(nitromethyl) sulphonyl]aniline in 180 ml of tetrahydrofuran. The reaction medium is refluxed for 8 hours. After addition of 2.5 ml (19.6 mmol) of benzenesulphonyl chloride, refluxing is continued for 6 h. A further 2.5 ml (19.6 mmol) of benzenesulphonyl chloride are added and refluxing is continued for 22 h. After cooling, the reaction medium is poured into 600 ml of water and is extracted with methylene chloride. These combined organic extracts are dried over sodium sulphate and concentrated to dryness under reduced pressure. The pasty residue obtained is purified by chromatography on a column of silica (eluent: methylene chloride) and crystallization from a mixture of hexane and methylene chloride to give 6.2 g (41%) of N-[3,5-dimethyl-4-[(nitromethyl)sulphonyl]phenylbenzenesulphonamide.

m.p.=129–131° C. (hexane/methylene chloride)
Elemental analysis: $C_{15}H_{16}N_2O_6S_2$ (M=384.41)

| | C % | H % | N % | S % |
|---|---|---|---|---|
| calculated | 46.86 | 4.20 | 7.29 | 16.68 |
| found | 47.16 | 4.14 | 7.38 | 16.87 |

IR: $\bar{v}$=3241, 1594, 1558, 1474, 1349, 1322, 1160, 1140, 1090, 601 cm$^{-1}$ $^1$H NMR (DMSO-d$_6$): δ=2.52 (6H, s); 6.50 (2H, s, exchangeable with CF$_3$COOD); 7.04 (2H, s); 7.63–7.72 (3H, m); 7.94–7.97 (2H, m); 11.16 (1H, s, exchangeable with CF$_3$COOD).

The 3,5-dimethyl-4-[(nitromethyl)sulphonyl]aniline starting material is obtained by carrying out, in order, steps 1 to 5 below:

Step 1

251.2 g (3.30 mol) of ammonium thiocyanate are rapidly added to a solution, maintained under a nitrogen atmosphere, of 121.2 g (1 mol) of 3,5-dimethylaniline in 1.75 l of anhydrous N,N-dimethylformamide. The temperature rises from 18 to 35° C. One and a half hours later, the temperature of the solution having returned to room temperature, 263.3 g (1.65 mol) of anhydrous cupric sulphate are added rapidly. The reaction medium is left stirring at room temperature for 3 days and is then poured into 8 l of water. The pH is brought to 7.5 by addition of 550 g (6.55 mol) of sodium bicarbonate. The medium is then filtered, the solid part being washed with ethyl acetate and the liquid part being extracted with ethyl acetate. The combined organic liquid phases are washed with 500 ml of water, dried over sodium sulphate and concentrated to dryness under reduced pressure. The pasty residue obtained is crystallized from 500 ml of hexane to give 128.8 g (72%) of 4-amino-2,6-dimethylphenyl thiocyanate which is used in the next step without further purification.

IR: $\bar{v}$=3483, 3382, 2142, 1627, 1591, 1470, 1435, 1342, 1191, 856, 850 cm$^{-1}$ $^1$H NMR (DMSO d$_6$): δ=2.58 (6H, s); 5.86 (2H, s); 6.65 (2H, s, exchangeable with CF$_3$COOD).

Step 2

46.9 g (463 mmol) of triethylamine are added rapidly to a mixture, maintained under a nitrogen atmosphere, of 75.2 g (422 mmol) of 4-amino-2,6-dimethylphenyl thiocyanate in 500 ml of anhydrous methylene chloride, followed by dropwise addition of 32.8 g (418 mmol) of acetyl chloride. The temperature rises to 41° C. and a precipitate forms. The next day, the reaction medium is poured into 400 ml of water. The insoluble part is isolated by filtration, washed with 100 ml of methylene chloride and dried. 61.8 g (67%) of an irritant and lachrymatory beige-coloured solid melting at 204–206° C. are obtained, consisting essentially of 4-acetamido-2,6-dimethylphenyl thiocyanate, which is used in the next step without further purification.

IR: $\bar{v}$=1670, 1595, 1541, 1401, 1369, 1325, 1261 cm$^{-1}$ $^1$H NMR (DMSO d$_6$): δ=2.08 (3H, s); 2.52 (6H, s), 7.54 (2H, s); 10.13 (1H, s, exchangeable with CF$_3$COOD).

Step 3

9.4 g (174 mmol) of sodium methoxide are added rapidly to a solution, maintained under a nitrogen atmosphere, of 6.95 ml (128 mmol) of nitromethane in 140 ml of anhydrous N,N-dimethylformamide. The temperature rises spontaneously to 35° C., and the reaction medium is then brought to 40° C. and maintained at this temperature for 1 h. After cooling to room temperature, a solution of 12.9 g (58.6 mmol) of 4-acetamido-2,6-dimethylphenyl thiocyanate in 140 ml of anhydrous of N,N-dimethylformamide is added dropwise over 1 hour 20 min. The mixture is stirred for 20 hours at room temperature and then poured into 1 l of water. The solution obtained, of about pH 10, is washed with twice 500 ml of ethyl acetate and then neutralized to pH 7 with dilute hydrochloric acid. This neutral aqueous solution is extracted with 4 times 500 ml of ethyl acetate. The organic extracts are dried over sodium sulphate and concentrated to dryness under reduced pressure. The solid residue obtained is purified by chromatography on a column of silica (eluent: 2/1 methylene chloride/ethyl acetate) to give 8.3 g (56%) of a solid melting at 160–163° C., consisting essentially of N-[3,5-dimethyl-4[(nitromethyl)thio]phenyl]acetamide.

IR: $\overline{v}$=1666, 1599, 1554, 1554 cm$^{-1}$ $^1$H NMR (DMSO d$_6$): δ=2.10 (3H, s); 2.46 (6H, s); 5.69 (2H, s); 7.47 (2H, s); 10.03 (1H, s, exchangeable with CF$_3$COOD).

Step 4

A solution, heated to 50° C., of 18.6 g (118 mmol) of potassium permanganate in 500 ml of water is added rapidly to a solution of 10.0 g (39.3 mmol) of N-[3,5-dimethyl-4-[(nitromethyl)thio]phenyl]acetamide in 1 l of acetic acid. The reaction medium is maintained at 65° C. for 30 min and is then cooled to room temperature in an ice bath. Saturated aqueous sodium metabisulphite solution is then added until decolorization has taken place (about 25 ml). The mixture is poured into 2.5 l of water and stirred for 1 h. The solid formed is separated out by filtration, rinsed with water and dried to give 6.1 g (54%) of a white solid melting at 180–182° C., consisting essentially of N-[3,5-dimethyl-4-[(nitromethyl)sulphonyl]phenyl]acetamide which is used in the next step without further purification.

IR: $\overline{v}$=1677, 1595, 1559, 1534, 1382, 1367, 1330, 1315, 1260, 1152, 871, 746, 639, 615 cm$^{-1}$ $^1$H NMR (DMSO d$_6$): δ=2.25 (3H, s); 2.71 (6H, s); 6.64 (2H, s, exchangeable with CF$_3$COOD); 7.68 (2H, s); 10.48 (1H, s, exchangeable with CF$_3$COOD).

Step 5

A mixture of 13.1 g (45.8 mmol) of N-[3,5-dimethyl-4-[(nitromethyl)sulphonyl]phenyl]acetamide and 10.6 g (265 mmol) of sodium hydroxide pellets in 150 ml of water is maintained at 80° C. for 1 h. After cooling, the reaction medium is poured into 850 ml of water. Acidification to pH 5 with acetic acid (about 20 ml) causes the precipitation of a solid which is isolated by filtration. This solid is washed with twice 50 ml of water and dried to give 10.6 g (95%) of a beige-coloured solid melting at 128–130° C., consisting essentially of 3,5-dimethyl-4-[(nitromethyl)sulphonyl] aniline, which is used in the next step without further purification.

An analytical sample is obtained by recrystallization from a mixture of hexane and ethyl acetate.

m.p.=130–132° C.

Elemental analysis: C$_9$H$_{12}$N$_2$O$_4$S (M=244.26)

|  | C % | H % | N % | S % |
| --- | --- | --- | --- | --- |
| calculated | 44.25 | 4.95 | 11.47 | 13.13 |
| found | 44.24 | 4.95 | 11.55 | 13.15 |

IR: $\overline{v}$=3472, 3374, 1630, 1600, 1550, 1341, 1317, 1154, 726 cm$^{-1}$ $^1$H NMR (DMSO d$_6$): δ=2.40 (6H, s); 6.23 (4H, s, exchangeable with CF$_3$COOD); 6.35 (2H, s).

EXAMPLE 2

(Method A2)

N-[3,5-Dimethyl-4-[(nitromethyl)sulphonyl]phenyl] benzenesulphonamide 1.08 g (6.11 mmol) of benzenesulphonyl chloride are added rapidly to a mixture, maintained under a nitrogen atmosphere, of 1.0 g (4.09 mmol) of 3,5-dimethyl-4-[(nitromethyl)sulphonyl]aniline and 0.65 g (8.22 mmol) of pyridine, dried over potassium hydroxide, in 19 ml of anhydrous tetrahydrofuran. The reaction medium is stirred for 2 h at room temperature. The next day, it is poured into a mixture of water and ice and acidified with 1N hydrochloric acid. The mixture is then extracted with methylene chloride. The combined organic extracts are washed with water, dried over sodium sulphate and concentrated to dryness under reduced pressure.

The oily residue obtained is purified by chromatography on a column of silica (eluent: methylene chloride) and crystallization from a mixture of hexane and methylene chloride, to give 1.1 g (70%) of N-[3,5-dimethyl-4-[(nitromethyl)sulphonyl]phenyl]benzenesulphonamide which is identical in all respects to the compound obtained in Example 1.

EXAMPLE 3

(Method D)

N-[3,5-Dimethyl-4-[(nitromethyl)thio]phenyl] benzenesulphonamide 0.75 g (7.49 mmol) of calcium carbonate and then 1.0 g (5.66 mmol) of benzenesulphonyl chloride are added to a solution, maintained under a nitrogen atmosphere, of 0.80 g (3.77 mmol) of 3,5-dimethyl-4-[(nitromethyl)thio]aniline in 30 ml of anhydrous tetrahydrofuran. After stirring for 3 days at room temperature, the reaction medium is poured into water and extracted with methylene chloride. The combined organic extracts are washed with water, dried over sodium Sulphate and concentrated to dryness under reduced pressure. The residue obtained is purified by chromatography on a column of silica (eluent: methylene chloride) to give 0.9 g (68%) of N-[3,5-dimethyl-4-[(nitromethyl)thio]phenyl] benzenesulphonamide.

m.p.=146–148° C. (hexane/ethyl acetate)

Elemental analysis: C$_{15}$H$_{16}$N$_2$O$_4$S$_2$ (M=352.41)

|  | C % | H % | N % | S % |
| --- | --- | --- | --- | --- |
| calculated | 51.12 | 4.58 | 7.95 | 18.19 |
| found | 50.95 | 4.54 | 8.03 | 18.05 |

IR: $\overline{v}$=3275, 1596, 1554, 1474, 1467, 1379, 1323, 1163, 1092, 872, 688 cm$^{-1}$ $^1$H NMR (DMSO d$_6$): δ=2.26 (6H, s); 5.53 (2H, s); 6.85 (2H, s); 7.48–7.60 (3H, m); 7.74–7.77 (2H, m); 10.46 (1H, s, exchangeable with CF$_3$COOD).

The 3,5-dimethyl-4-[(nitromethyl)thio]aniline starting material is obtained according to the following procedure:

A mixture of 1.6 g (6.29 mmol) of N-[3,5-dimethyl-4-[(nitromethyl)thio]phenyl]acetamide and 1.44 g (36.0 mmol) of sodium hydroxide pellets in 20 ml of water is maintained at 80° C. for 1 h. After cooling, the reaction medium is poured into water and extracted twice with ethyl acetate. The combined organic extracts are dried over sodium sulphate and concentrated to dryness under reduced pressure. The residue obtained is purified by chromatography on a column of silica (eluent: 2/1 hexane/ethyl acetate) to give 0.8 g (60%) of an oil consisting of 3,5-dimethyl-4-[(nitromethyl)thio]aniline.

$^1$H NMR (DMSO $d_6$): δ=2.31 (6H, s); 5.43 (2H, s, exchangeable with $CF_3COOD$); 5.52 (2H, s); 6.39 (2H, s).

EXAMPLE 4

(Method E)

N-[3,5-Dimethyl-4-[(nitromethyl)sulphinyl]phenyl]benzenesulphonamide 1.3 g (5.46 mmol) of 70–75% m-chloroperbenzoic acid are added rapidly to a solution of 2.2 g (6.24 mmol) of N-[3,5-dimethyl-4-[(nitromethyl)thio]phenyl]benzenesulphonamide in 79 ml of anhydrous chloroform. The reaction medium is stirred for 24 h at room temperature and then poured into a solution of 0.33 g (3.93 mmol) of sodium bicarbonate. The mixture is extracted with methylene chloride. The combined organic extracts are dried over sodium sulphate and concentrated to dryness under reduced pressure. The residue obtained is purified by successive chromatographies on a column of silica (eluent for the first chromatography: methylene chloride; eluent for the second chromatography: 2/1 hexane/ethyl acetate) and crystallization from hexane, to give 0.98 g (42%) of N-[3,5-dimethyl-4-[(nitromethyl)sulphinyl]phenyl]benzenesulphonamide.

m.p. >50° C. (decomposition at 130° C.)

Elemental analysis: $C_{15}H_{16}N_2O_5S_2$ (M=368.41)

|  | C % | H % | N % | S % |
| --- | --- | --- | --- | --- |
| calculated | 48.90 | 4.38 | 7.60 | 17.40 |
| found | 48.96 | 4.66 | 7.47 | 17.58 |

IR: $\bar{v}$=1595, 1557, 1160, 1091, 1074, 602 cm$^{-1}$ $^1$H NMR (DMSO $d_6$): δ=2.43 (6H, s); 6.14 (2H, s, exchangeable with $CF_3COOD$); 6.88 (2H, s); 7.57–7.66 (3H, m); 7.85–7.88 (2H, m); 10.79 (1H, s, exchangeable with $CF^3COOD$).

EXAMPLE 5

(Method A1)

4-Chloro-N-[3,5-dimethyl-4-[(nitromethyl)sulphonyl]phenyl]benzenesulphonamide 1.45 g (14.5 mmol) of calcium carbonate and then 2.3 g (10.9 mmol) of 4-chlorobenzenesulphonyl chloride are successively added to a mixture of 1.8 g (7.37 mmol) of 3,5-dimethyl-4-[(nitromethyl)sulphonyl]aniline in 45 ml of anhydrous tetrahydrofuran. The reaction medium is stirred for 27 h at room temperature and then poured into 200 ml of water. This mixture is extracted 3 times with methylene chloride. The combined organic extracts are washed with water, dried over sodium sulphate and concentrated to dryness under reduced pressure. The residue obtained is purified by chromatography on a column of silica (eluent: methylene chloride) and then by recrystallization from chloroform, to give 0.44 g (14%) of 4-chloro-N-[3,5-dimethyl-4-[(nitromethyl)sulphonyl]phenyl]benzenesulphonamide.

m.p. 160–162° C. (chloroform)

Elemental analysis: $C_{15}H_{15}ClN_2O_6S_2$ (M=418.86)

|  | C % | H % | N % |
| --- | --- | --- | --- |
| calculated | 43.01 | 3.61 | 6.69 |
| found | 42.99 | 3.59 | 6.72 |

IR: $\bar{v}$=1594, 1562, 1346, 1167, 1147, 621 cm$^{-1}$ $^1$H NMR (DMSO d6): δ=2.48 (6H, s); 6.46 (2H, s, exchangeable with $CF_3COOD$); 6.99 (2H, s); 7.67–7.72 (2H, m); 7.89–7.93 (2H, m); 11.18 (1H, s, exchangeable with $CF_3COOD$).

EXAMPLE 6

(Method A2)

N-[3,5-Dimethyl-4-[(nitromethyl)sulphonyl]phenyl]-3-methylbenzenesulphonamide 1.3 ml (16.1 mmol) of pyridine, dried over potassium hydroxide, and 2.3 g (12.1 mmol) of 3-methylbenzenesulphonyl chloride are successively added to a solution, maintained under a nitrogen atmosphere, of 2.0 g (8.19 mmol) of 3,5-dimethyl-4-[(nitromethyl]sulphonyl]aniline in 50 ml of anhydrous tetrahydrofuran. The reaction medium is stirred for 24 h at room temperature and then maintained at 40° C. for 1 h, after which it is poured into a mixture of 100 ml of water and 100 g of ice. This mixture is acidified to pH 3 by addition of 1N hydrochloric acid and is extracted with 3 times 100 ml of methylene chloride. The combined organic extracts are washed with 100 ml of water, dried over sodium sulphate and concentrated to dryness under reduced pressure. The residue obtained is purified by chromatography on a column of silica (eluent: methylene chloride) to give 2.3 g (71%) of N-[3,5-dimethyl-4-[(nitromethyl)sulphonyl]phenyl]-3-methylbenzenesulphonamide.

m.p. 179–181° C. (hexane/ethyl acetate)

Elemental analysis: $C_{16}H_{18}N_2O_6S_2$ (M=398.44)

|  | C % | H % | N % | S % |
| --- | --- | --- | --- | --- |
| calculated | 48.23 | 4.55 | 7.03 | 16.09 |
| found | 48.21 | 4.61 | 7.06 | 15.99 |

IR: $\bar{v}$=3244, 1594, 1565, 1339, 1308, 1182, 1159, 1148, 607 cm$^{-1}$ $^1$H NMR (DMSO $d_6$): δ=2.38 (3H, s); 2.48 (6H, s); 6.45 (2H, s, exchangeable with $CF_3COOD$); 6.99 (2H, s); 7.48–7.53 (2H, m); 7.69–7.72 (2H, m); 11.05 (1H, s, exchangeable with $CF_3COOD$).

EXAMPLE 7

(Method A2)

N-[3,5-Dimethyl-4-[(nitromethyl)sulphonyl]phenyl]-4-methylbenzenesulphonamide

The title compound is obtained by working as in Example 6, using 2.3 g (12.1 mmol) of 4-methylbenzenesulphonyl chloride.

Duration of the heating at 40° C.: 3 h
Yield: 0.31 g (10%)
m.p.=163–165° C. (hexane/ethyl acetate)
Elemental analysis: $C_{16}H_{18}N_2O_6S_2$ (M=398.44)

|  | C % | H % | N % | S % |
|---|---|---|---|---|
| calculated | 48.23 | 4.55 | 7.03 | 16.09 |
| found | 48.27 | 4.66 | 6.97 | 15.83 |

IR: $\bar{\nu}$=3254, 1596, 1562, 1341, 1309, 1178, 1161, 1147, 1090, 1071, 664, 635, 599 cm$^{-1}$ $^1$H NMR (DMSO d$_6$): δ=2.36 (3H, s); 2.47 (6H, s); 6.45 (2H, s, exchangeable with CF$_3$COOD); 6.98 (2H, s); 7.41 (2H, d, J=8 Hz); 7.79 (2H, d, J=8 Hz); 11.03 (1H, s, exchangeable with CF$_3$COOD).

EXAMPLE 8

(Method A2)

2,4-Difluoro-N-[3,5-dimethyl-4-[(nitromethyl)sulphonyl]phenyl]benzenesulphonamide 0.65 g (8.22 mmol) of pyridine, dried over potassium hydroxide, and 1.3 g (6.11 mmol) of 2,4-difluorobenzenesulphonyl chloride are successively added to a solution, cooled to about 10° C., of 1.0 g (4.09 mmol) of 3,5-dimethyl-4-[(nitromethyl)sulphonyl]aniline in 20 ml of anhydrous tetrahydrofuran. The reaction medium is stirred for 2 h at 10° C. and then for 20 h at room temperature, after which it is poured into 100 ml of water. The mixture is brought to pH 3 by addition of concentrated hydrochloric acid and then extracted with methylene chloride. The combined organic extracts are washed with water, dried over sodium sulphate and concentrated to dryness under reduced pressure. The oily residue obtained is purified by chromatography on a column of silica (eluent: methylene chloride) and by recrystallization from toluene, to give 0.38 g (22%) of 2,4-difluoro-N-[3,5-dimethyl-4-[(nitromethyl)sulphonyl]phenyl]benzenesulphonamide.

m.p.=154–156° C. (toluene)

Elemental analysis: $C_{15}H_{14}F_2N_2O_6S_2$ (M=420.40)

|  | C % | H % | F % | N % | S % |
|---|---|---|---|---|---|
| calculated | 42.85 | 3.36 | 9.04 | 6.66 | 15.25 |
| found | 42.81 | 3.41 | 8.80 | 6.69 | 15.26 |

IR: $\bar{\nu}$=3261, 1599, 1559, 1478, 1339, 1165, 1149, 1124, 1075, 866, 672 cm$^{-1}$ $^1$H NMR (DMSO d$_6$): δ=2.48 (6H, s); 6.46 (2H, s, exchangeable with CF$_3$COOD); 6.98 (2H, s); 7.31–7.37 (1H, m); 7.54–7.62 (1H, m); 8.09–8.17 (1H, m); 11.49 (1H, s, exchangeable with CF$_3$COOD).

EXAMPLE 9

(Method A2)

N-[3,5-Dimethyl-4-[(nitromethyl)sulphonyl]phenyl]-3-(trifluoromethyl)benzenesulphonamide The title compound is obtained by working as in Example 6, using 3.0 g (12.3 mmol) of 3-(trifluoromethyl)benzenesulphonyl chloride.

Duration of the heating at 40° C.: 4 h
Yield: 1.7 g (46%)
m.p.=146–148° C. (hexane/ethyl acetate)
Elemental analysis: $C_{16}H_{15}F_3N_2O_6S_2$ (M=452.42)

|  | C % | H % | F % | N % | S % |
|---|---|---|---|---|---|
| calculated | 42.47 | 3.34 | 12.60 | 6.19 | 14.17 |
| found | 42.80 | 3.41 | 12.23 | 6.26 | 14.50 |

IR: $\bar{\nu}$=3244, 1593, 1569, 1359, 1344, 1326, 1182, 1167, 1148, 1139, 1104, 1071, 641 cm$^{-1}$ $^1$H NMR (DMSO d$_6$): δ=2.48 (6H, s); 6.67 (2H, s, exchangeable with CF$_3$COOD); 7.22 (2H, s); 8.09 (1H, t, J=7.8 Hz); 8.30 (1H, d, J=8 Hz); 8.38–8.43 (1H, m); 10.44 (1H, s, exchangeable with CF$_3$COOD).

EXAMPLE 10

(Method A2)

3,4-Difluoro-N-[3,5-dimethyl-4-[(nitromethyl)sulphonyl]phenyl]benzenesulphonamide The title compound is obtained by working as in Example 8, starting with a solution of 2.0 g (8.19 mmol) of 3,5-dimethyl-4-[(nitromethyl)sulphonyl]aniline in 40 ml of tetrahydrofuran, 1.3 g (16.4 mmol) of pyridine and 2.6 g (12.2 mmol) of 3,4-difluorobenzenesulphonyl chloride. The reaction medium is successively stirred for 1 h at 10° C., for 19 h at room temperature, for 3 h at 50° C. and for 16 h at room temperature.

Yield: 1.2 g (35%)

m.p.=158–160° C. (toluene)

Elemental analysis: $C_{15}H_{14}F_2N_2O_6S_2$ (M=420.40)

|  | C % | H % | F % | N % | S % |
|---|---|---|---|---|---|
| calculated | 42.85 | 3.36 | 9.04 | 6.66 | 15.25 |
| found | 42.72 | 3.33 | 8.83 | 6.73 | 15.37 |

IR: $\bar{\nu}$=3273, 1600, 1556, 1511, 1362, 1345, 1329, 1277, 1148, 1120, 1069, 637 cm$^{-1}$ $^1$H NMR (DMSO d$_6$): δ=2.37 (6H, s); 6.34 (2H, s, exchangeable with CF$_3$COOD); 6.89 (2H, s); 7.56–7.67 (2H, m); 7.86–7.92 (1H, m); 11.07 (1H, s, exchangeable with CF$_3$COOD).

EXAMPLE 11

(Method A2)

N-(3,5-Dimethyl-4-[(nitromethyl)sulphonyl]phenyl-4-methoxybenzenesulphonamide 1.33 ml (16.4 mmol) of pyridine, dried over potassium hydroxide, and 2.54 g (12.3 mmol) of 4-methoxybenzenesulphonyl chloride are successively added to a solution, maintained under a nitrogen atmosphere, of 2.0 g (8.19 mmol) of 3,5-dimethyl-4-[(nitromethyl)sulphonyl]aniline in 40 ml of anhydrous tetrahydrofuran. The reaction medium is stirred for 24 h at room temperature and is then maintained at 40° C. for 1 h, after which it is poured into a mixture of water and ice. The aqueous solution obtained is brought to pH 1 by addition of 1N hydrochloric acid and is extracted with methylene chloride. The combined organic extracts are washed with water, dried over sodium sulphate and concentrated to dryness under reduced pressure. The oily residue obtained is purified by chromatography on a column of silica (eluent: methylene chloride) and recrystallization from a mixture of hexane and ethyl acetate, to give 1.1 g (33%) of N-[3,5-dimethyl-4-[(nitromethyl)sulphonyl]phenyl]-4-methoxybenzenesulphonamide.

m.p.=141–142° C. (hexane/ethyl acetate)

Elemental analysis: $C_{16}H_{18}N_2O_7S_2$ (M=414.44)

|  | C % | H % | N % | S % |
|---|---|---|---|---|
| calculated | 46.37 | 4.38 | 6.76 | 15.47 |
| found | 46.40 | 4.38 | 6.89 | 15.22 |

IR: $\bar{v}$=3251, 1595, 1557, 1486, 1398, 1346, 1308, 1260, 1176, 1151, 1148, 1095, 1071, 874, 836, 599 cm$^{-1}$ $^1$H NMR (DMSO d$_6$): δ=2.58 (6H, s); 3.93 (3H, s); 6.56 (2H, s, exchangeable with CF$_3$COOD); 7.08 (2H, s); 7.20–7.25 (2H, m); 7.92–7.97 (2H, m); 11.07 (1H, s, exchangeable with CF$_3$COOD)

EXAMPLE 12

(Method A1)

4-Bromo-N-[3,5-dimethyl-4-[(nitromethyl)sulphonyl]phenyl]benzenesulphonamide 2.0 g (20.0 mmol) of calcium carbonate and 3.8 g (14.9 mmol) of 4-bromobenzenesulphonyl chloride are successively added to a mixture of 2.4 g (9.83 mmol) of 3,5-dimethyl-4-[(nitromethyl)sulphonyl]aniline in 45 ml of anhydrous tetrahydrofuran. The reaction medium is stirred for 20 h at room temperature and is then refluxed for 48 h. After cooling, it is poured into 400 ml of water and extracted with methylene chloride. The combined organic extracts are dried over sodium sulphate and concentrated to dryness under reduced pressure. The oily residue obtained is purified by chromatography on a column of silica (eluent: methylene chloride) to give 1.1 g (24%) of 4-bromo-N-[3,5-dimethyl-4-[(nitromethyl)sulphonyl]phenyl]benzenesulphonamide.

m.p.=164–166° C. (hexane/ethyl acetate)

Elemental analysis: $C_{15}H_{15}BrN_2O_6S_2$ (M=463.32)

|  | C % | H % | Br % | N % | S % |
|---|---|---|---|---|---|
| calculated | 38.88 | 3.26 | 17.25 | 6.05 | 13.84 |
| found | 39.07 | 3.38 | 17.00 | 5.93 | 13.70 |

IR: $\bar{v}$=3258, 1594, 1568, 1471, 1393, 1342, 1166, 1148, 1088, 1069, 740, 632, 609 cm$^{-1}$ $^1$H NMR (DMSO d$_6$): δ=2.64 (6H, s); 6.62 (2H, s, exchangeable with CF$_3$COOD); 7.14 (2H, s); 7.99 (4H, s); 11.34 (1H, s, exchangeable with CF$_3$COOD).

EXAMPLE 13

(Method A1)

3-Bromo-N-[3,5-dimethyl-4-[(nitromethyl)sulphonyl]phenyl]benzenesulphonamide

The title compound is obtained by working as in Example 12, using 3.8 g (14.9 mmol) of 3-bromobenzenesulphonyl chloride.

Duration of the reflux: 40 h

Yield: 0.8 g (18%)

m.p.=156–158° C. (hexane/ethyl acetate)

Elemental analysis: $C_{15}H_{15}BrN_2O_6S_2$ (M=463.32)

|  | C % | H % | Br % | N % |
|---|---|---|---|---|
| calculated | 38.88 | 3.26 | 17.25 | 6.05 |
| found | 39.17 | 3.45 | 17.00 | 5.91 |

IR: $\bar{v}$=3237, 1594, 1565, 1483, 1397, 1358, 1340, 1181, 1167, 1148, 1071, 885, 679, 635, 605 cm$^{-1}$ $^1$H NMR (DMSO d$_6$): δ=2.64 (6H, s); 6.62 (2H, s, exchangeable with CF$_3$COOD); 7.15 (2H, s); 7.70–7.75 (1H, m); 8.04–8.07 (2H, m); 8.18–8.19 (1H, m); 11.33 (1H, s, exchangeable with CF$_3$COOD).

EXAMPLE 14

(Method A2)

N-[3,5-Dimethyl-4-[(nitromethyl)sulphonyl]phenyl]-2-(trifluoromethyl)benzenesulphonamide The title compound is obtained by working as in Example 6, starting with a solution of 2.0 g (8.19 mmol) of 3,5-dimethyl-4-[(nitromethyl)sulphonyl]aniline in 38 ml of tetrahydrofuran, 1.32 ml (16.3 mmol) of pyridine and 3.0 g (12.3 mmol) of 2-(trifluoromethyl)benzenesulphonyl chloride.

Durations of the heating at 40° C.: 8 h

Yield: 0.7 g (19%)

m.p.=171–173° C. (hexane/ethyl acetate)

Elemental analysis: $C_{16}H_{15}F_3N_2O_6S_2$ (M=452.42)

|  | C % | H % | F % | N % | S % |
|---|---|---|---|---|---|
| calculated | 42.47 | 3.34 | 12.60 | 6.19 | 14.17 |
| found | 42.61 | 3.35 | 12.32 | 6.21 | 14.55 |

IR: $\bar{v}$=3370, 3028, 2954, 1596, 1562, 1405, 1348, 1340, 1307, 1180, 1166, 1149, 1122 cm$^{-1}$ $^1$H NMR (DMSO d$_6$): δ=2.42 (6H, s); 6.41 (2H, s, exchangeable with CF$_3$COOD); 6.93 (2H, s); 7.82–7.91 (2H, m); 7.96–8.01 (1H, m); 8.17–8.20 (1H, m); 11.38 (1H, s, exchangeable with CF$_3$COOD).

EXAMPLE 15

(Method A2)

N-[3,5-Dimethyl-4-[(nitromethyl)sulphonyl]phenyl]-2-naphthalenesulphonamide 1.3 ml (16.1 mmol) of pyridine, dried over potassium hydroxide, and 2.8 g (12.4 mmol) of 2-naphthalenesulphonyl chloride are successively added to a solution, maintained under a nitrogen atmosphere, of 2.0 g (8.19 mmol) of 3,5-dimethyl-4-[(nitromethyl)sulphonyl]aniline in 40 ml of anhydrous tetrahydrofuran. The reaction medium is stirred for 6 h at room temperature and is then left to stand for 2 days, after which it is poured into 200 ml of water. The mixture is brought to pH 1 with dilute hydrochloric acid and is extracted twice with methylene chloride.

The combined organic extracts are washed twice with water, dried over sodium sulphate and concentrated to dryness under reduced pressure.

The solid residue obtained is purified by chromatography on a column of silica (eluent: methylene chloride) to give 3.0 g (84%) of N-[3,5-dimethyl-4-[(nitromethyl)sulphonyl]phenyl]-2-naphthalenesulphonamide.

m.p.=208–215° C. (ethyl acetate)-decomposition at about 215° C.

Elemental analysis: $C_{19}H_{18}N_2O_6S_2$ (M=434.47)

|  | C % | H % | N % | S % |
|---|---|---|---|---|
| calculated | 52.52 | 4.18 | 6.45 | 14.76 |
| found | 52.62 | 4.29 | 6.45 | 14.42 |

IR: $\bar{v}$=3230, 1557, 1340, 1180, 1163, 1148, 1072, 659, 641 cm$^{-1}$ $^1$H NMR (DMSO d$_6$): δ=2.54 (6H, s); 6.50 (2H, s, exchangeable with CF$_3$COOD); 7.13 (2H, s); 7.76–7.81 (2H, m); 7.91–7.95 (1H, m); 8.10–8.33 (3H, m); 8.77–8.78 (1H, m); 11.30 (1H, s, exchangeable with CF$_3$COOD).

EXAMPLE 16

(Method A2)

N-[3,5-Dimethyl-4-[(nitromethyl)sulphonyl]phenyl] (2-nitrophenyl)methanesulphonamide The title compound is obtained by working as in Example 15, using 2.9 g (12.3 mmol) of (2-nitrophenyl)methanesulphonyl chloride.

Duration of the stirring at room temperature: 26 h

Yield: 2.6 g (72%)

m.p.=189–190° C. (hexane/ethyl acetate)

Elemental analysis: $C_{16}H_{17}N_3O_8S_2$ (M=443.44)

|  | C % | H % | N % | S % |
|---|---|---|---|---|
| calculated | 43.33 | 3.86 | 9.48 | 14.46 |
| found | 43.67 | 3.82 | 9.60 | 14.32 |

IR: $\bar{v}$=3243, 1596, 1562, 1531, 1487, 1399, 1361, 1336, 1313, 1160, 1147, 1140, 902, 869, 632 cm$^{-1}$ $^1$H NMR (DMSO d$_6$): δ=2.58 (6H, s); 5.21 (2H, s); 6.56 (2H, s, exchangeable with CF$_3$COOD); 6.98 (2H, s); 7.61–7.64 (1H, m); 7.70–7.80 (2H, m); 8.10–8.13 (1H, m); 10.83 (1H, s, exchangeable with CF$_3$COOD).

EXAMPLE 17

(Method A2)

2-Bromo-N-[3,5-dimethyl-4-[(nitromethyl)sulphonyl]-phenyl]benzenesulphonamide

The title compound is obtained by working as in Example 15, using 2.5 g (9.78 mmol) of 2-bromobenzenesulphonyl chloride.

The reaction medium is stirred for 20 h at room temperature, an additional 0.6 g (2.35 mmol) of 2-bromobenzenesulphonyl chloride is then added and stirring is continued for 4 h at room temperature.

Yield: 1.6 g (42%)

m.p.=140–142° C. (hexane/ethyl acetate)

Elemental analysis: $C_{15}H_{15}BrN_2O_6S_2$ (M=463.32)

|  | C % | H % | Br % | N % |
|---|---|---|---|---|
| calculated | 38.88 | 3.26 | 17.25 | 6.05 |
| found | 39.07 | 3.15 | 17.25 | 6.05 |

IR: $\bar{v}$=3295, 3041, 2969, 1595, 1562, 1478, 1337, 1192, 1188, 1144, 1071, 632, 601 cm$^{-1}$ $^1$H NMR (DMSO d$_6$): δ=2.54 (6H, s); 6.54 (2H, s, exchangeable with CF$_3$COOD); 7.03 (2H, s); 7.66–7.77 (2H, m); 7.93–7.96 (1H, m); 8.33–8.37 (1H, m); 1153 (1H, s, exchangeable with CF$_3$COOD).

EXAMPLE 18

(Method A2)

N-[3,5-Dimethyl-4-[(nitromethyl)sulphonyl]phenyl]-4-(methylsulphonyl)benzenesulphonamide 1.31 ml (16.2 mmol) of pyridine, dried over potassium hydroxide, and 2.5 g (9.82 mmol) of 4-(methylsulphonyl)benzenesulphonyl chloride are successively added to a solution, maintained under a nitrogen atmosphere, of 1.6 g (6.55 mmol) of 3,5-dimethyl-4-[(nitromethyl)sulphonyl]aniline in 50 ml of anhydrous tetrahydrofuran. The reaction medium is stirred for 2 days at room temperature and then poured into 200 ml of water. The mixture obtained is brought to pH 3 by addition of 1N hydrochloric acid and is then extracted with 3 times 200 ml of ethyl acetate. The combined organic extracts are washed with water, dried over sodium sulphate and concentrated to dryness under reduced pressure. The residue is purified by chromatography on a column of silica (eluent: 2/1 methylene chloride/ethyl acetate) and recrystallization from a mixture of hexane and ethyl acetate, to give 0.78 g (26%) of N-[3,5-dimethyl-4-[(nitromethyl)sulphonyl]phenyl]-4-(methylsulphonyl)benzenesulphonamide.

m.p.=192–194° C. (hexane/ethyl acetate)

Elemental analysis: $C_{16}H_{18}N_2O_8S_3$ (M=462.50)

|  | C % | H % | N % | S % |
|---|---|---|---|---|
| calculated | 41.55 | 3.92 | 6.06 | 20.80 |
| found | 41.39 | 4.02 | 5.90 | 20.76 |

IR: $\bar{v}$=3281, 1597, 1586, 1555, 1485, 1401, 1395, 1366, 1349, 1328, 1306, 1294, 1289, 1165, 1150, 1090, 1072, 877, 860, 741, 624 cm$^{-1}$ $^1$H NMR (DMSO d$_6$): δ=2.49 (6H, s); 3.30 (3H, s); 6.46 (2H, s, exchangeable with CF$_3$COOD); 7.02 (2H, s); 8.16 (4H, s); 11.35 (1H, s, exchangeable with CF$_3$COOD).

EXAMPLE 19

(Method A2)

(E)-N-[3,5-Dimethyl-4-[(nitromethyl)sulphonyl]phenyl]styrenesulphonamide

The title compound is obtained by working as in Example 18, starting with a solution of 2.0 g (8.19 mmol) of 3,5- dimethyl-4-[(nitromethyl)sulphonyl]aniline in 50 ml of tetrahydrofuran, 1.31 ml (16.2 mmol) of pyridine and 2.5 g (12.3 mmol) of trans-β-styrenesulphonyl chloride.

The reaction medium is stirred for 3 days at room temperature and is extracted with methylene chloride.

Yield: 1.5 g (45%)

m.p.=174–176° C. (hexane/ethyl acetate)

Elemental analysis: $C_{17}H_{18}N_2O_6S_2$ (M=410.45)

|  | C % | H % | N % | S % |
|---|---|---|---|---|
| calculated | 49.74 | 4.42 | 6.83 | 15.62 |
| found | 50.06 | 4.45 | 6.84 | 15.35 |

IR: $\bar{v}$=3235, 1610, 1595, 1577, 1555, 1475, 1390, 1357, 1345, 1323, 1164, 1141, 1067, 889, 872, 744, 627 cm$^{-1}$ $^1$H NMR (DMSO d$_6$): δ=2.67 (6H, s); 6.64 (2H, s, exchangeable with CF$_3$COOD); 7.22 (2H, s); 7.58–7.63 (4H, m); 7.87–7.97 (3H, m); 11.04 (1H, s, exchangeable with CF$_3$COOD).

EXAMPLE 20

(Method C)

1-[3,5-Dimethyl-4-[(nitromethyl)sulphonyl]phenyl]-3-[(2-methylphenyl)sulphonyl]urea A solution of 0.77 ml (5.09 mmol) of o-toluenesulphonyl isocyanate in 7.7 ml of anhydrous methylene chloride is added dropwise to a suspension, maintained under a nitrogen atmosphere, of 1.3 g (5.32 mmol) of 3,5-dimethyl-4-[(nitromethyl)sulphonyl]aniline in 25.6 ml of anhydrous methylene chloride. The temperature of the reaction medium rises spontaneously by 7° C. A precipitate forms in the solution initially obtained. Stirring is continued for 1 hour at room temperature and the solid is then isolated by filtration and washed with hexane to give 1.9 g (yield=86%) of 1-[3,5-dimethyl-4-[(nitromethyl)sulphonyl]phenyl]-3-[(2-methylphenyl)sulphonyl]urea.

m.p.=194–196° C. (hexane/ethyl acetate)

Elemental analysis: $C_{17}H_{19}N_3O_7S_2$ (M=441.47)

|  | C % | H % | N % | S % |
|---|---|---|---|---|
| calculated | 46.25 | 4.34 | 9.52 | 14.52 |
| found | 46.40 | 4.44 | 9.31 | 14.34 |

IR: $\bar{v}$=3303, 1654, 1587, 1565, 1526, 1455, 1393, 1362, 1341, 1326, 1164, 1153, 1131, 1089, 898, 883, 707, 606 cm$^{-1}$ $^1$H NMR (DMSO d$_6$): δ=2.46 (6H, s); 2.58 (3H, s); 6.41 (2H, s, exchangeable with CF$_3$COOD); 7.24 (2H, s); 7.38–7.43 (2H, m); 7.52–7.57 (1H, m); 7.94 (1H, d, J=8 Hz); 9.02 (1H, s, exchangeable with CF$_3$COOD); 11.14 (1H, broad peak, exchangeable with CF$_3$COOD).

EXAMPLE 21

(Method C)

1-[3,5-Dimethyl-4-[(nitromethyl)sulphonyl]phenyl]-3-[(4-methylphenyl)sulphonyl]urea A solution of 1.55 ml (10.2 mmol) of p-toluenesulphonyl isocyanate in 15.5 ml of anhydrous methylene chloride is added dropwise to a suspension, maintained under a nitrogen atmosphere, of 2.6 g (10.6 mmol) of 3,5-dimethyl-4-[(nitromethyl)sulphonyl]aniline in 52 ml of anhydrous methylene chloride. The temperature of the reaction medium rises spontaneously by 2° C. Stirring of the solution obtained is continued for 30 minutes at room temperature. The reaction medium is then concentrated to dryness under reduced pressure; the residue is purified by chromatography on a column of silica (eluent: methylene chloride and then a 9/1 methylene chloride/methanol mixture) and crystallization from methylene chloride, to give 2.5 g (57%) of 1-[3,5-dimethyl-4-[(nitromethyl)sulphonyl]phenyl]-3-[(4-methylphenyl)sulphonyl]urea.

m.p. 150–155° C.

Elemental analysis: $C_{17}H_{19}N_3O_7S_2$ (M=441.47)

|  | C % | H % | N % | S % |
|---|---|---|---|---|
| calculated | 46.25 | 4.34 | 9.52 | 14.52 |
| found | 46.40 | 4.44 | 9.31 | 14.12 |

IR: $\bar{v}$=1594, 1562, 1337, 1263, 1247, 1159, 1136 cm$^{-1}$ $^1$H NMR (DMSO d$_6$): δ=2.37 (3H, s); 2.55 (6H, s); 6.45 (2H, s, exchangeable with CF$_3$COOD); 7.38 (2H, d, J=8 Hz); 7.42 (2H, s); 7.83 (2H, d, J=8 Hz); 9.12 (1H, s, exchangeable with CF$_3$COOD).

EXAMPLE 22

(Method A1)

N-[4-[3,5-Dimethyl-4-[(nitromethyl)sulphonyl]phenylsulphamoyl]phenyl]acetamide 2.9 g (12.4 mmol) of N-acetylsulphanilyl chloride are added portionwise to a mixture, maintained under a nitrogen atmosphere, of 2.0 g (8.19 mmol) of 3,5-dimethyl-4-[(nitromethyl)sulphonyl]aniline and 1.6 g (16.0 mmol) of calcium carbonate in 40 ml of anhydrous tetrahydrofuran. The reaction medium is stirred for 6 h at room temperature and is then refluxed for 2 h, after which it is poured into 200 ml of water. The mixture is extracted 3 times with methylene chloride. The combined organic extracts are washed with water, dried over sodium sulphate and concentrated to dryness under reduced pressure. The oily residue obtained is crystallized by trituration from a mixture of hexane and ethyl acetate. These crystals are washed with a mixture of methylene chloride and methanol at room temperature and then with a mixture of hexane and ethyl acetate at reflux, and finally with ethanol at room temperature, to give 0.26 g (7.2%) of N-[4-[3,5-dimethyl-4-[(nitromethyl)sulphonyl]phenylsulphamoyl]phenyl]acetamide.

m.p.=209–210° C.

Elemental analysis: $C_{17}H_{19}N_3O_7S_2$ (M=441.47)

|  | C % | H % | N % | S % |
|---|---|---|---|---|
| calculated | 46.25 | 4.34 | 9.52 | 14.52 |
| found | 46.25 | 4.43 | 9.78 | 14.25 |

IR: $\bar{v}$=3382, 3190, 1676, 1592, 1550, 1536, 1340, 1156, 1147 cm$^{-1}$ $^1$H NMR (DMSO d$_6$): δ=2.10 (3H, s); 2.51 (6H, s); 6.48 (2H, s, exchangeable with CF$_3$COOD); 7.01 (2H, s);

7.78–7.81 (2H, m); 7.86–7.89 (2H, m); 10.39 (1H, s, exchangeable with CF$_3$COOD); 11.03 (1H, s, exchangeable with CF$_3$COOD).

EXAMPLE 23

(Method A2)

N-[3,5-Dimethyl-4-[(nitromethyl)sulphonyl]phenyl]-2,2,2-trifluoroethanesulphonamide The title compound is obtained by working as in Example 18, starting with a solution of 1.5 g (6.14 mmol) of 3,5-dimethyl-4-[(nitromethyl)sulphonyl]aniline in 50 ml of tetrahydrofuran, 0.97 ml (12.0 mmol) of pyridine and 1.0 ml (9.04 mmol) of 2,2,2-trifluoroethanesulphonyl chloride.

The chromatography eluent is methylene chloride.

Yield: 1.6 g (68%).

m.p.=168–170° C. (hexane/ethyl acetate)

Elemental analysis: C$_{11}$H$_{13}$F$_3$N$_2$O$_6$S$_2$ (M=390.35)

|            | C %   | H %  | F %   | N %  | S %   |
|------------|-------|------|-------|------|-------|
| calculated | 33.84 | 3.36 | 14.60 | 7.18 | 16.43 |
| found      | 34.14 | 3.44 | 14.25 | 7.35 | 16.19 |

IR: $\bar{\nu}$=3227, 1601, 1564, 1351, 1333, 1323, 1270, 1248, 1157, 1147, 1135, 1089 cm$^{-1}$ $^1$H NMR (DMSO d$_6$): δ=2.44 (6H, s); 4.73 (2H, q, J=10 Hz); 6.39 (2H, s, exchangeable with CF$_3$COOD); 6.96 (2H, s); 11.04 (1H, s, exchangeable with CF$_3$COOD).

EXAMPLE 24

(Method A1)

N-[3,5-Dimethyl-4-[(nitromethyl)sulphonyl]phenyl]-4-fluorobenzenesulphonamide 1.65 g (16.5 mmol) of calcium carbonate are added to a solution of 2.0 g (8.19 mmol) of 3,5-dimethyl-4-[(nitromethyl)sulphonyl]aniline in 40 ml of anhydrous tetrahydrofuran, followed by portionwise addition of 2.4 g (12.3 mmol) of 4-fluorobenzenesulphonyl chloride. The reaction medium is refluxed for 50 hours. After cooling, it is poured into 200 ml of water and extracted with 3 times 100 ml of methylene chloride. The combined organic extracts are washed with 100 ml of water, dried over sodium sulphate and concentrated to dryness under reduced pressure. The oily residue obtained is purified by chromatography on a column of silica (eluent: methylene chloride) and recrystallization from a mixture of hexane and ethyl acetate, to give 1.2 g (36%) of N-[3,5-dimethyl-4-[(nitromethyl)sulphonyl]phenyl]-4-fluorobenzenesulphonamide.

m.p.=152–154° C. (hexane/ethyl acetate)

Elemental analysis: C$_{15}$H$_{15}$FN$_2$O$_6$S$_2$ (M=402.41)

|            | C %   | H %  | F %  | N %  | S %   |
|------------|-------|------|------|------|-------|
| calculated | 44.77 | 3.76 | 4.72 | 6.96 | 15.93 |
| found      | 44.76 | 3.85 | 4.43 | 6.93 | 15.84 |

IR: $\bar{\nu}$=1592, 1563, 1478, 1398, 1362, 1341, 1177, 1169, 1159, 1146, 1090, 1071, 877, 865, 841, 666, 635 cm$^{-1}$ $^1$H NMR (DMSO d$_6$): δ=2.68 (6H, s); 6.48 (2H, s, exchangeable with CF$_3$COOD); 7.18 (2H, s); 7.61–7.69 (2H, m); 8.13–8.19 (2H, m); 1131 (1H, s, exchangeable with CF$_3$COOD).

EXAMPLE 25

(Method A2)

N-[3,5-Dimethyl-4-[(nitromethyl)sulphonyl]phenyl]-3-fluorobenzenesulphonamide

The title compound is obtained as in Example 6, starting with a solution of 2.0 g (8.19 mmol) of 3,5-dimethyl-4-[(nitromethyl)sulphonyl]aniline in 40 ml of tetrahydrofuran, 1.29 g (16.3 mmol) of pyridine and 2.4 g (12.3 mmol) of 3-fluorobenzenesulphonyl chloride.

The reaction medium is stirred for 2 h at room temperature and then for 6 h at 40° C.

Yield: 1.3 g (40%).

m.p.=135–137° C. (hexane/ethyl acetate)

Elemental analysis: C$_{15}$H$_{15}$FN$_2$O$_6$S$_2$ (M=402.41)

|            | C %   | H %  | F %  | N %  | S %   |
|------------|-------|------|------|------|-------|
| calculated | 44.77 | 3.76 | 4.72 | 6.96 | 15.93 |
| found      | 44.62 | 3.63 | 4.65 | 6.91 | 16.21 |

IR: $\bar{\nu}$=3263, 1597, 1557, 1551, 1479, 1395, 1357, 1343, 1320, 1307, 1230, 1168, 1146, 1072, 856, 695, 676, 636, 610 cm$^{-1}$ $^1$H NMR (DMSO d$_6$): δ=2.45 (6H, s); 6.43 (2H, s, exchangeable with CF$_3$COOD); 6.97 (2H, s); 7.50–7.73 (4H, m); 11.16 (1H, s, exchangeable with CF$_3$COOD)

EXAMPLE 26

(Method A2)

N-[3,5-Dimethyl-4-[(nitromethyl)sulphonyl]phenyl] phenylmethanesulphonamide

The title compound is obtained by working as in Example 11, starting with a solution of 3.0 g (12.3 mmol) of 3,5-dimethyl-4-[(nitromethyl)sulphonyl]aniline in 57 ml of tetrahydrofuran, 2.0 ml (24.7 mmol) of pyridine and 3.5 g (18.4 mmol) of phenylmethanesulphonyl chloride.

The reaction medium is stirred for 20 h at room temperature and then for 5 h at 40° C. The final product is crystallized from a mixture of hexane and methylene chloride.

Yield: 0.42 g (8.6%)

m.p.=124–126° C. (hexane/methylene chloride)

Elemental analysis: C$_{16}$H$_{18}$N$_2$O$_6$S$_2$ (M=398.44)

|            | C %   | H %  | N %  | S %   |
|------------|-------|------|------|-------|
| calculated | 48.23 | 4.55 | 7.03 | 16.09 |
| found      | 48.49 | 4.59 | 7.03 | 16.04 |

IR: $\bar{\nu}$=3256, 1596, 1566, 1488, 1405, 1359, 1337, 1325, 1312, 1144, 1071, 697, 638 cm$^{-1}$ $^1$H NMR (DMSO d$_6$): δ=2.72 (6H, s); 4.90 (2H, s); 6.69 (2H, s, exchangeable with CF$_3$COOD); 7.14 (2H, s); 7.49–7.58 (5H, m); 10.70 (1H, s, exchangeable with CF$_3$COOD)

EXAMPLE 27

(Method A2)

4-Bromo-2,5-difluoro-N-[3,5-dimethyl-4-[(nitromethyl)sulphonyl]phenyl]benzenesulphonamide 1.3 g (16.4 mmol) of pyridine, dried over potassium hydroxide, and then 3.6 g (12.3 mmol) of 4-bromo-2,5-difluorobenzenesulphonyl chloride are added to a solution, maintained under a nitrogen atmosphere, of 2.0 g (8.19 mmol) of 3,5-dimethyl-4-[(nitromethyl)sulphonyl]aniline in 40 ml of anhydrous tetrahydrofuran. The reaction medium is stirred for 7 h 30 min at room temperature and then for 11 h at reflux; after cooling, it is poured into 300 ml of water and extracted 3 times with methylene chloride. The combined organic extracts are washed with water, dried over sodium sulphate and concentrated to dryness under reduced pressure. The solid residue obtained is purified by chromatography on a column of silica (eluent: methylene chloride) and recrystallization from a mixture of hexane and ethyl acetate, to give 0.24 g (6.2%) of 4-bromo-2,5-difluoro-N-[3,5-dimethyl-4-[(nitromethyl)sulphonyl]phenyl]benzenesulphonamide, containing 5 mol % of ethyl acetate.

m.p.=167–169° C. (hexane/ethyl acetate)

Elemental analysis: $C_{15}H_{13}BrF_2N_2O_6S_2$ (M=499.31), 5% $C_4H_8O_2$

|            | C %   | H %  | Br %  | F %  | N %  | S %   |
|------------|-------|------|-------|------|------|-------|
| calculated | 36.24 | 2.68 | 15.86 | 7.54 | 5.56 | 12.73 |
| found      | 36.50 | 2.75 | 15.47 | 7.39 | 5.51 | 12.80 |

IR: $\bar{v}$=3242, 1565, 1480, 1350, 1167 cm$^{-1}$ $^1$H NMR (DMSO $d_6$): δ=2.42 (6H, s); 6.39 (2H, s, exchangeable with CF$_3$COOD); 6.92 (2H, s); 7.97–8.03 (2H, m); 11.55 (1H, s, exchangeable with CF$_3$COOD)

EXAMPLE 28

(Method A2)

2,5-Difluoro-N-[3,5-dimethyl-4-[(nitromethyl)sulphonyl]phenyl]benzenesulphonamide The title compound is obtained by working as in Example 15, using 2.6 g (12.2 mmol) of 2,5-difluorobenzenesulphonyl chloride.

The reaction medium is stirred for 20 h at room temperature and is then left to stand for 5 days before working up. The final product is purified by chromatography on a column of silica (eluent: methylene chloride) and recrystallization from toluene.

Yield: 1.1 g (32%)

m.p.=132–134° C. (toluene)

Elemental analysis: $C_{15}H_{14}F_2N_2O_6S_2$ (M=420.40)

|            | C %   | H %  | F %  | N %  | S %   |
|------------|-------|------|------|------|-------|
| calculated | 42.85 | 3.36 | 9.04 | 6.66 | 15.25 |
| found      | 43.09 | 3.43 | 9.05 | 6.69 | 15.40 |

IR: $\bar{v}$=1562, 1486, 1353, 1159, 1147, 607 cm$^{-1}$ $^1$H NMR (DMSO $d_6$): δ=2.47 (6H, s); 6.44 (2H, s, exchangeable with CF$_3$COOD); 6.99 (2H, s); 7.49–7.57 (1H, m); 7.60–7.64 (1H, m); 7.86–7.92 (1H, m)

The starting material, 2,5-difluorobenzenesulphonyl chloride, is obtained according to the following procedure:

12.9 g (99.9 mmol) of 2,5-difluoroaniline are added rapidly to a mixture, cooled to below −10° C. by a bath of cardice in ethanol, of 33 ml of concentrated hydrochloric acid and 10 ml of acetic acid, followed by dropwise addition of a solution of 7.4 g (107 mmol) of sodium nitrite in 15 ml of water. Stirring is continued for 45 min after the end of the addition, at a temperature between −10 and −25° C.

This solution, maintained at about −25° C., is added portionwise to a mixture, cooled to 10° C. in an ice bath, obtained by saturation of 100 ml of acetic acid with sulphur dioxide and addition of 2.5 g (25.3 mmol) of cuprous chloride. Considerable evolution of nitrogen is produced. The reaction medium is allowed to return to room temperature and is maintained at that temperature for 2 h, after which it is poured into 450 ml of a mixture of water and ice; it is extracted with ethyl ether. The combined ether extracts are washed with saturated aqueous sodium bicarbonate solution, dried over sodium sulphate and concentrated. The oily residue obtained is distilled under reduced pressure to give 14.3 g (87%) of a liquid consisting essentially of 2,5-difluorobenzenesulphonyl chloride, which is used in the next step without further purification.

b.p.=65–70° C. at 0.5 mm of mercury

IR: $\bar{v}$=3118, 3087, 1488, 1410, 1384, 1301, 1255, 1202, 1188, 1152, 1119, 1052, 881, 832, 772, 692, 689, 605, 599 cm$^{-1}$ $^1$H NMR (CDCl$_3$) δ=7.28–7.32 (1H, m); 7.38–7.42 (1H, m); 7.58–7.63 (1H, m)

EXAMPLE 29

(Method A2)

2,3-Difluoro-N-[3,5-dimethyl-4-[(nitromethyl)sulphonyl]phenyl]benzenesulphonamide The title compound is obtained by working as in Example 15, using 2.6 g (12.2 mmol) of 2,3-difluorobenzenesulphonyl chloride.

The reaction medium is stirred for 20 h at room temperature, in the absence of light, and left to stand for 3 days before working up. The final product is purified by chromatography on a column of silica (eluent: methylene chloride) and recrystallization from toluene.

Yield: 1.1 g (32%)

m.p.=166–168° C. (toluene)

Elemental analysis: $C_{15}H_{14}F_2N_2O_6S_2$ (M=420.40)

|            | C %   | H %  | F %  | N %  | S %   |
|------------|-------|------|------|------|-------|
| calculated | 42.85 | 3.36 | 9.04 | 6.66 | 15.25 |
| found      | 43.07 | 3.51 | 8.98 | 6.61 | 15.01 |

IR: $\bar{v}$=3292, 1600, 1557, 1494, 1363, 1348, 1329, 1276, 1199, 1161, 1140, 636 cm$^{-1}$ $^1$H NMR (DMSO $d_6$): δ=2.29 (6H, s); 6.28 (2H, s, exchangeable with CF$_3$COOD); 6.81 (2H, s); 7.24–7.29 (1H, m); 7.61–7.67 (2H, m); 11.44 (1H, s, exchangeable with CF$_3$COOD).

The starting material, 2,3-difluorobenzenesulphonyl chloride, is obtained according to the procedure described in Example 28, using, on the one hand, 22 ml of concentrated hydrochloric acid, 7.7 ml of acetic acid, 10.0 g (77.5 mmol) of 2,3-difluoroaniline and 5.8 g (84.1 mmol) of sodium nitrite in 12 ml of water, and, on the other hand, 77 ml of acetic acid saturated with sulphur dioxide and 1.9 g (19.2 mmol) of cuprous chloride.

Yield: 8.5 g (52%)

b.p.=60–80° C. at 0.5 mm of mercury

IR: $\bar{v}$1606, 1493, 1388, 1280, 1238, 1203, 1171, 1148, 907, 824, 789, 711, 650 cm$^{-1}$ $^1$H NMR (CDCl$_3$): δ=7.37–7.42 (1H, m) ; 7.61–7.65 (1H, m); 7.76–7.81 (1H, m)

EXAMPLE 30

(Method A2)

3,5-Difluoro-N-[3,5-dimethyl-4-[(nitromethyl)sulphonyl]phenyl]benzenesulphonamide The title compound is obtained by working as in Example 15, using 2.6 g (12.2 mmol) of 3,5-difluorobenzenesulphonyl chloride, which is added as a solution in 20 ml of tetrahydrofuran.

The reaction medium is stirred for 20 h at room temperature, in the absence of light, and is left to stand for 3 days before working up. The final product is purified by chromatography on a column of silica (eluent: methylene chloride) and recrystallization from toluene.

Yield: 1.8 g (52%)

m.p.=187–190° C. (toluene)

Elemental analysis: C$_{15}$H$_{14}$F$_2$N$_2$O$_6$S$_2$ (M=420.40)

|  | C % | H % | F % | N % | S % |
| --- | --- | --- | --- | --- | --- |
| calculated | 42.85 | 3.36 | 9.04 | 6.66 | 15.25 |
| found | 43.21 | 3.44 | 8.85 | 6.50 | 15.01 |

IR: $\bar{v}$=3343, 2979, 1607, 1595, 1555, 1474, 1446, 1401, 1363, 1346, 1316, 1295, 1252, 1196, 1160, 1127, 1070, 993, 801, 668, 637, 616 cm$^{-1}$ $^1$H NMR (DMSO d$_6$): δ=2.45 (6H, s); 6.42 (2H, s, exchangeable with CF$_3$COOD); 6.97 (2H, s); 7.57–7.64 (3H, m); 11.21 (1H, s, exchangeable with CF$_3$COOD)

The starting material, 3,5-difluorobenzenesulphonyl chloride, is obtained according to the procedure described in Example 28, using, on the one hand, 22 ml of concentrated hydrochloric acid, 7.7 ml of acetic acid, 10.0 g (77.5 mmol) of 3,5-difluoroaniline and 5.8 g (84.1 mmol) of sodium nitrite in 15 ml of water, and, on the other hand, 77 ml of acetic acid saturated with sulphur dioxide and 1.9 g (19.2 mmol) of cuprous chloride.

Yield: 7.1 g (43%)-white solid b.p.=60–120° C. at 0.9 mm of mercury

IR: $\bar{v}$=3100, 1608, 1592, 1446, 1375, 1361, 1301, 1178, 1133, 1080, 992, 881, 866, 662, 611 cm$^{-1}$ $^1$H NMR (CDCl$_3$): δ=7.04–7.11 (1H, m) ; 7.46–7.48 (2H, m)

EXAMPLE 31

(Method A2)

N-[3,5-Dimethyl-4-[(nitromethyl)sulphonyl]phenyl]-1-naphthalenesulphonamide

The title compound is obtained by working as in Example 15, using 2.8 g (12.4 mmol) of 1-naphthalenesulphonyl chloride.

The reaction medium is stirred for 26 h at room temperature. The final product is purified by chromatography on a column of silica (eluent: methylene chloride) and recrystallization from toluene.

Yield: 1.4 g (39%)

m.p.=170–172° C. (toluene)

Elemental analysis: C$_{19}$H$_{18}$N$_2$O$_6$S$_2$ (M=434.47)

|  | C % | H % | N % | S % |
| --- | --- | --- | --- | --- |
| calculated | 52.52 | 4.18 | 6.45 | 14.76 |
| found | 52.65 | 3.89 | 6.51 | 14.72 |

IR: $\bar{v}$=3267, 1595, 1560, 1330, 1181, 1163, 1136, 1070, 771, 636, 600 cm$^{-1}$ $^1$H NMR (DMSO d$_6$): δ=2.44 (6H, s); 6.42 (2H, s, exchangeable with CF$_3$COOD); 6.95 (2H, s); 7.68–7.83 (3H, m); 8.13 (1H, d, J=8.0 Hz); 8.31 (1H, d, J=8.2 Hz); 8.46 (1H, d, J=7.3 Hz); 8.70 (1H, d, J=8.5 Hz); 11.53 (1H, s, exchangeable with CF$_3$COOD)

EXAMPLE 32

(Method A2)

N-[3,5-Dimethyl-4-[(nitromethyl)sulphonyl]phenyl]-2-thiophenesulphonamide

The title compound is obtained by working as in Example 6, starting with a mixture of 3.0 g (12.3 mmol) of 3,5-dimethyl-4-[(nitromethyl)sulphonyl]aniline, 60 ml of tetrahydrofuran and 1.95 ml (24.1 mmol) of pyridine, to which are rapidly added 2.8 g (15.3 mmol) of 2-thiophenesulphonyl chloride.

The reaction medium is stirred for 24 h at room temperature and heated at 50° C. for 4 h. The final product is purified by chromatography on a column of silica (eluent: methylene chloride) and recrystallization from toluene.

Yield: 0.8 g (17%)

m.p.=158–159° C. (toluene)

Elemental analysis: C$_{13}$H$_{14}$N$_2$O$_6$S$_3$ (M=390.44)

|  | C % | H % | N % | S % |
| --- | --- | --- | --- | --- |
| calculated | 39.99 | 3.61 | 7.18 | 24.63 |
| found | 40.07 | 3.68 | 7.29 | 24.46 |

IR: $\bar{v}$=1598, 1552, 1345, 1151, 600 cm$^{-1}$ $^1$H NMR (DMSO d$_6$): δ=2.36 (6H, s); 6.33 (2H, s, exchangeable with CF$_3$COOD); 6.90 (2H, s); 7.02–7.04 (1H, m); 7.63–7.65 (1H, m); 7.83–7.85 (1H, m); 11.09 (1H, s, exchangeable with CF$_3$COOD)

EXAMPLE 33

(Method B)

N-[4-[(Dichloronitromethyl)sulphonyl]-3,5-dimethylphenyl]benzenesulphonamide

A mixture of 0.96 g (2.50 mmol) of N-[3,5-dimethyl-4-[(nitromethyl)sulphonyl]phenyl]benzenesulphonamide, 0.66 g (4.94 mmol) of N-chlorosuccinimide and 10 mg (0.06 mmol) of 2,2'-azobisisobutyronitrile in 20 ml of carbon tetrachloride is refluxed for 6 h. After cooling, the insoluble part is removed by filtration and the solution is concentrated to dryness under reduced pressure. The pasty residue obtained is purified by chromatography on a column of silica (eluent: methylene chloride) and crystallization from a mixture of hexane and methylene chloride, to give 0.28 g (25%) of N-[4-[(dichloronitromethyl)sulphonyl]-3,5-dimethylphenyl]benzenesulphonamide.

m.p.=112–114° C. (hexane/methylene chloride)

Elemental analysis: $C_{15}H_{14}Cl_2N_2O_6S_2$ (M=453.31)

|  | C % | H % | Cl % | N % | S % |
|---|---|---|---|---|---|
| calculated | 39.74 | 3.11 | 15.64 | 6.18 | 14.14 |
| found | 40.24 | 3.20 | 15.71 | 6.29 | 13.70 |

IR: $\bar{v}$=3218, 1580, 1466, 1360, 1329, 1310, 1186, 1161, 1091, 748, 618, 609, 601 cm$^{-1}$ $^1$H NMR (DMSO d$_6$): δ=2.38 (6H, s); 7.00 (2H, s); 7.49–7.59 (3H, m); 7.81–7.84 (2H, m); 11.29 (1H, s, exchangeable with CF$_3$COOD)

EXAMPLE 34

(Method A2)

N-[3,5-Dimethyl-4-[(nitromethyl)sulphonyl]phenyl]-2-fluorobenzenesulphonamide 1.29 g (16.3 mmol) of pyridine, dried over potassium hydroxide, and 2.4 g (12.3 mmol) of 2-fluorobenzenesulphonyl chloride are rapidly and successively added to a solution, maintained under a nitrogen atmosphere, of 2.0 g (8.19 mmol) of 3,5-dimethyl-4-[(nitromethyl)sulphonyl]aniline in 40 ml of anhydrous tetrahydrofuran. The mixture is stirred for 2 h at room temperature and is then maintained at 40° C. for 12 h. After cooling, the reaction medium is poured into a mixture of 100 ml of water and 100 g of ice, it is acidified with 1N hydrochloric acid to pH 2 and is then extracted with 3 times 100 ml of methylene chloride. The combined organic extracts are washed with 100 ml of water, dried over sodium sulphate and concentrated to dryness under reduced pressure. The pasty residue obtained is purified by chromatography on a column of silica (eluent: methylene chloride) and recrystallization from a mixture of hexane and ethyl acetate, to give 1.5 g (yield=46%) of N-[3,5-dimethyl-4-[(nitromethyl)sulphonyl]phenyl]-2-fluorobenzenesulphonamide.

m.p.=175–177° C. (hexane/ethyl acetate)

Elemental analysis: $C_{15}H_{15}FN_2O_6S_2$ (M=402.41)

|  | C % | H % | F % | N % | S % |
|---|---|---|---|---|---|
| calculated | 44.77 | 3.76 | 4.72 | 6.96 | 15.93 |
| found | 44.99 | 3.61 | 4.66 | 6.95 | 15.81 |

IR: $\bar{v}$=3236, 1598, 1583, 1557, 1475, 1390, 1350, 1329, 1191, 1175, 1160, 1149, 1124, 1077, 1068, 890, 881, 875, 778, 623, 600 cm$^{-1}$ $^1$H NMR (DMSO d$_6$): δ=2.56 (6H, s); 6.55 (2H, s, exchangeable with CF$_3$COOD); 7.08 (2H, s); 7.51–7.56 (2H, m); 7.84–7.87 (1H, m); 8.11–8.16 (1H, m); 11.55 (1H, s, exchangeable with CF$_3$COOD)

EXAMPLE 35

(Method A2)

N-[3,5-Dimethyl-4-[(nitromethyl)sulphonyl]phenyl]-4-(trifluoromethyl)benzenesulphonamide The title compound is obtained by working as in Example 34, using 3.0 g (12.3 mmol) of 4-(trifluoromethyl)benzenesulphonyl chloride. The reaction medium is stirred for 2 h at room temperature and is then heated at 40° C. for 20 h.

Yield: 1.5 g (35%)

m.p. 187–188° C. (hexane/ethyl acetate)

Elemental analysis: $C_{16}H_{15}F_3N_2O_6S_2$ (M=452.42)

|  | C % | H % | F % | N % | S % |
|---|---|---|---|---|---|
| calculated | 42.47 | 3.34 | 12.60 | 6.19 | 14.17 |
| found | 42.73 | 3.39 | 12.42 | 6.13 | 14.00 |

IR: $\bar{v}$=3252, 1596, 1563, 1408, 1347, 1324, 1166, 1140, 1131, 1092, 1062, 751, 638 cm$^{-1}$ $^1$H NMR (DMSO d$_6$): δ=2.42 (6H, s); 6.40 (2H, s, exchangeable with CF$_3$COOD); 6.95 (2H, s); 7.95 (2H, d, J=8.4 Hz); 8.05 (2h, d, J=8.3 Hz); 11.26 (1H, s, exchangeable with CF$_3$COOD).

|  | C % | H % | F % | N % | S % |
|---|---|---|---|---|---|
| calculated | 37.98 | 2.34 | 20.03 | 5.91 | 13.52 |
| found | 37.94 | 2.38 | 19.65 | 5.75 | 13.40 |

IR: $\bar{v}$=1563, 1522, 1503, 1330, 1170, 1142, 992 cm$^{-1}$ $^1$H NMR (DMSO d$_6$): δ=2.49 (6H, s); 6.50 (2H, s, exchangeable with CF$_3$COOD); 7.03 (2H, s); 12.1 (broad peak, exchangeable with CF$_3$COOD)

EXAMPLE 38

(Method A2)

N-[3,5-Dimethyl-4-[(nitromethyl)sulphonyl]phenyl]-2-dibenzofuransulphonamide

The title compound is obtained by working as in Example 6, starting with a solution of 2.0 g (8.19 mmol) of 3,5-dimethyl-4-[(nitromethyl)sulphonyl]aniline in 38 ml of tetrahydrofuran, 1.3 ml (16.1 mmol) of pyridine and 3.3 g (12.3 mmol) of 2-dibenzofuransulphonyl chloride [prepared according to M. Janczewski and H. Maziarczyk, Rocz. Chem. 47 (11), 2055–2069 (1973)].

The reaction medium is stirred for 20 h at room temperature and is then heated at 45° C. for 4 h. The final product is purified by chromatography on a column of silica (eluent: methylene chloride) and recrystallization from a mixture of hexane and ethyl acetate.

Yield: 0.48 g (12%)
m.p.=214–215° C. (hexane/ethyl acetate) (decomp.)
Elemental analysis: $C_{21}H_{18}N_2O_7S_2$ (M=474.49)

|  | C % | H % | N % | S % |
|---|---|---|---|---|
| calculated | 53.15 | 3.82 | 5.90 | 13.51 |
| found | 52.88 | 3.91 | 5.92 | 13.46 |

IR: $\bar{\nu}$=3284, 1596, 1571, 1479, 1471, 1446, 1400, 1361, 1336, 1324, 1310, 1205, 1199, 1160, 1139, 1129, 1069, 884, 852, 755, 637, 611 cm$^{-1}$ $^1$H NMR (DMSO d$_6$): δ=2.41 (6H, s); 3.36 (2H, s, exchangeable with CF$_3$COOD); 7.00 (2H, s); 7.43 (1H, t, J=7.2 Hz); 7.53–7.59 (1H, m); 7.72 (1H, d, J=8.3 Hz); 7.88 (1H, d, J=8.7 Hz); 7.95–7.99 (1H, m); 8.32 (1H, d, J=7.3 Hz); 8.82 (1H, d, J=1.9 Hz); 11.10 (1H, s, exchangeable with CF$_3$COOD).

EXAMPLE 36

(Method A2)

N-[3,5-Dimethyl-4-[(nitromethyl)sulphonyl]phenyl]-4-(trifluoromethoxy)benzenesulphonamide The title compound is obtained by working as in Example 11, starting with a solution of 3.1 g (12.7 mmol) of 3,5-dimethyl-4-[(nitromethyl)sulphonyl]aniline in 62.4 ml of tetrahydrofuran, 2.05 g (25.9 mmol) of pyridine and 5.0 g (19.2 mmol) of 4-(trifluoromethoxy)benzenesulphonyl chloride.

Yield: 1.8 g (29%)
m.p.=180–182° C. (hexane/ethyl acetate)
Elemental analysis: $C_{16}H_{15}F_3N_2O_7S_2$ (M=468.42)

|  | C % | H % | F % | N % | S % |
|---|---|---|---|---|---|
| calculated | 41.02 | 3.23 | 12.17 | 5.98 | 13.69 |
| found | 41.06 | 3.29 | 11.81 | 6.13 | 13.41 |

IR: $\bar{\nu}$=1595, 1559, 1347, 1327, 1266, 1218, 1164, 1138 cm$^{-1}$ $^1$H NMR (DMSO d$_6$): δ=2.34 (6H, s); 6.31 (2H, s, exchangeable with CF$_3$COOD); 6.85 (2H, s); 7.47 (2H, d, J=8.2 Hz); 7.87–7.92 (2H, m); 11.07 (1H, s, exchangeable with CF$_3$COOD).

EXAMPLE 37

(Method A1)

N-[3,5-Dimethyl-4-[(nitromethyl)sulphonyl]phenyl]-2,3,4,5,6-pentafluorobenzenesulphonamide The title compound is obtained working as in Example 5, starting with a solution of 1.3 g (5.32 mmol) of 3,5-dimethyl-4-[(nitromethyl)sulphonyl]aniline in 50 ml of tetrahydrofuran, 1.1 g (11.0 mmol) of calcium carbonate and 2.1 g (7.88 mmol) of pentafluorobenzenesulphonyl chloride. The reaction medium is stirred for 68 h at room temperature. The final product is purified by chromatography on a column of silica (eluent: methylene chloride).

Yield: 0.4 g (16%)
m.p.=128–130° C. (hexane/methylene chloride)
Elemental analysis: $C_{15}H_{11}F_5N_2O_6S_2$ (M=474.37)

EXAMPLE 39

(Method A2)

N-[3,5-Dimethyl-4-[(nitromethyl)sulphonyl]phenyl]-4-biphenylsulphonamide

The title compound is obtained by working as in Example 6, starting with a solution of 2.0 g (8.19 mmol) of 3,5-dimethyl-4-[(nitromethyl)sulphonyl]aniline in 38 ml of tetrahydrofuran, 1.3 ml (16.1 mmol) of pyridine and 3.1 g (12.3 mmol) of 4-biphenylsulphonyl chloride.

The reaction medium is stirred for 20 h at room temperature and heated to 40° C. for 4 h. The final product is purified by chromatography on a column of silica (eluent: methylene chloride) and recrystallization from a mixture of hexane and ethyl acetate.

Yield: 0.68 g (18%)
m.p.=206–208° C. (hexane/ethyl acetate) (decomp.)
Elemental analysis: $C_{21}H_{20}N_2O_6S_2$ (M=460.51)

|  | C % | H % | N % | S % |
|---|---|---|---|---|
| calculated | 54.77 | 4.38 | 6.08 | 13.92 |
| found | 54.90 | 4.43 | 6.05 | 13.58 |

IR: $\bar{\nu}$=3237, 1594, 1564, 1557, 1479, 1346, 1156, 1068, 764, 674, 626, 604 cm$^{-1}$ $^1$H NMR (DMSO d$_6$): δ=2.53 (6H, s); 6.49 (2H, s, exchangeable with CF$_3$COOD); 7.08 (2H, s); 7.48–7.57 (3H, m); 7.75–7.78 (2H, m); 7.94–8.04 (4H, m); 11.20 (1H, s, exchangeable with CF$_3$COOD).

EXAMPLE 40

(Method A2)

N-[3,5-Dimethyl-4-[(nitromethyl)sulphonyl]phenyl]methanesulphonamide

A solution of 1.7 g (14.8 mmol) of methanesulphonyl chloride in 5 ml of anhydrous tetrahydrofuran is added dropwise to a solution, maintained under a nitrogen atmosphere, of 2.7 g (11.0 mmol) of 3,5-dimethyl-4-[(nitromethyl)sulphonyl]aniline and 1.6 g (20.2 mmol) of pyridine, dried over potassium hydroxide, in 50 ml of anhydrous tetrahydrofuran. The mixture is stirred for 6 h 30 min at room temperature and is then refluxed for 4 h. 1.1 g (9.60 mmol) of methanesulphonyl chloride are then added and refluxing is continued for 1 h 30 min. A further 1.1 g (9.60 mmol) of methanesulphonyl chloride are added and refluxing is continued for 4 h. After cooling, the reaction medium is poured into ice-cold water and extracted with methylene chloride. The combined organic extracts are dried over sodium sulphate and concentrated to dryness under reduced pressure. The residue obtained is crystallized from a cooled mixture of hexane and methylene chloride and is purified by recrystallization from a mixture of hexane and ethyl acetate, to give 1.1 g (yield=22%) of N-[3,5-dimethyl-4-[(nitromethyl)sulphonyl]phenyl]methanesulphonamide containing 14 mol % of ethyl acetate.

m.p.=138–140° C. (hexane/ethyl acetate)

Elemental analysis: $C_{10}H_{14}N_2O_6S_2$ (M=322.35), 14% $C_4H_8O_2$

|  | C % | H % | N % | S % |
|---|---|---|---|---|
| calculated | 38.18 | 4.61 | 8.32 | 19.05 |
| found | 37.90 | 4.55 | 8.12 | 18.62 |

IR: $\bar{v}$=3269, 1598, 1569, 1344, 1339, 1309, 1142 cm$^{-1}$ $^1$H NMR (DMSO d$_6$): δ=2.58 (6H, s); 3.23 (3H, s); 3.5 (1H, broad peak, exchangeable with CF$_3$COOD); 6.52 (2H, s, exchangeable with CF$_3$COOD); 7.09 (2H, s).

EXAMPLE 41

(Method C)

1-[3,5-Dimethyl-4-[(nitromethyl)sulphonyl]phenyl]-3-(phenylsulphony)urea

The title compound is obtained by working as in Example 20, starting with a suspension of 2.8 g (11.5 mmol) of 3,5-dimethyl-4-[(nitromethyl)sulphonyl]aniline in 56 ml of methylene chloride and a solution of 2.0 g (10.9 mmol) of benzenesulphonyl isocyanate in 15 ml of methylene chloride.

The residual ethyl acetate is eliminated from the final product by refluxing in methylene chloride for 2 h.

Yield: 4.5 g (96%)

m.p.=140–142° C. (hexane/ethyl acetate)

Elemental analysis: $C_{16}H_{17}N_3O_7S_2$ (M=427.44)

|  | C % | H % | N % | S % |
|---|---|---|---|---|
| calculated | 44.96 | 4.01 | 9.83 | 15.00 |
| found | 45.15 | 4.16 | 10.15 | 14.71 |

IR: $\bar{v}$=1658, 1587, 1567, 1529, 1463, 1326, 1152, 1086, 899 cm$^{-1}$ $^1$H NMR (DMSO d$_6$): δ=2.31 (6H, s); 6.26 (2H, s, exchangeable with CF$_3$COOD); 7.09 (2H, s); 7.41–7.54 (3H, m); 7.76–7.79 (2H, m); 9.06 (1H, s, exchangeable with CF$_3$COOD); 10.96 (1H, broad peak exchangeable with CF$_3$COOD)

EXAMPLE 42

(Method A2)

N-[3,5-Dimethyl-4-[(nitromethyl)sulphonyl]-3-dibenzofuransulphonamide

The title compound is obtained by working as in Example 6, starting with a solution of 2.0 g (8.19 mmol) of 3,5-dimethyl-4-[(nitromethyl)sulphonyl]aniline in 40 ml of tetrahydrofuran, 1.29 g (16.3 mmol) of pyridine and 3.0 g (12.3 mmol) of 3-dibenzofuransulphonyl chloride [prepared according to M. Janczewski and H. Maziarczyk, Rocz. Chem. 48 (11), 1907–1919 (1974)]. The reaction medium is stirred for 2 h at room temperature and is then heated at 40° C. for 24 h. The final product is purified by chromatography on a column of silica (eluent: methylene chloride) and recrystallization from a mixture of hexane and ethyl acetate.

Yield: 2.1 g (54%)

m.p.=206–208° C. (hexane/ethyl acetate)

Elemental analysis: $C_{21}H_{18}N_2O_7S_2$ (M=474.49)

|  | C% | H% | N% |
|---|---|---|---|
| calculated | 53.15 | 3.82 | 5.90 |
| found | 53.34 | 3.95 | 5.68 |

IR: $\bar{v}$=3274, 1592, 1561, 1462, 1343, 1324, 1201, 1180, 1158, 1139, 1068, 852, 745, 705, 653, 632 cm$^{-1}$ $^1$H NMR (DMSO d$_6$): δ=2.52 (6H, s); 6.46 (2H, s, exchangeable with CF$_3$COOD); 7.09 (2H, s); 7.53–7.55 (1H, m); 7.69–7.72 (1H, m); 7.84 (1H, d, J=8.3 Hz); 7.96–8.00 (1H, m); 8.28–8.33 (2H, m); 8.44 (1H, d, J=8.1 Hz); 11.25 (1H, s, exchangeable with CF$_3$COOD).

EXAMPLE 43

(Method A1)

N-[2-Chloro-4-[3,5-dimethyl-4-[(nitromethyl)sulphonyl]phenylsulphamoyl]phenyl]acetamide The title compound is obtained by working as in Example 22, using 3.3 g (12.3 mmol) of 4-acetamido-3-chlorobenzenesulphonyl chloride.

The reaction medium is stirred for 7 h 30 min at room temperature and is then refluxed for 7 h 30 min. The solid residue obtained after concentration under reduced pressure is triturated from hexane and then washed with a mixture of hexane and ethyl acetate, and finally washed with ethanol.

Yield: 0.1 g (2.6%)

m.p.=209–211° C.

Elemental analysis: $C_{17}H_{18}ClN_3O_7S_2$ (M=475.92)

|  | C % | H % | Cl % | N % | S % |
|---|---|---|---|---|---|
| calculated | 42.90 | 3.81 | 7.45 | 8.83 | 13.47 |
| found | 42.75 | 3.91 | 7.75 | 8.77 | 13.01 |

IR: $\bar{v}$=3402, 3276, 1722, 1583, 1550, 1514, 1349, 1174, 1163, 631 cm$^{-1}$ $^1$H NMR (DMSO d$_6$): δ=2.04 (3H, s); 2.39 (6H, s); 6.36 (2H, s, exchangeable with CF$_3$COOD); 6.90 (2H, s); 7.74 (1H, dd, J=8.7 and 2.2 Hz); 7.86 (1H, d, J=2.2 Hz); 8.01 (1H, d, J=8.7 Hz); 9.64 (1H, s, exchangeable with CF$_3$COOD)

EXAMPLE 44

(Method A2)

N-[3,5-Dimethyl-4-[(nitromethyl)sulphonyl]phenyl-2-methoxybenzenesulphonamide

The title compound is obtained by working as in Example 18, starting with a solution of 2.0 g (8.19 mmol) of 3,5-dimethyl-4-[(nitromethyl)sulphonyl]aniline in 50 ml of tetrahydrofuran, 1.31 ml (16.2 mmol) of pyridine and 2.53 g (12.2 mmol) of 2-methoxybenzenesulphonyl chloride [prepared according to H. Meerwein et al., Chem. Ber. 90, 841–852 (1957)]

The final product is purified by chromatography on a column of silica (eluent: methylene chloride).

Yield: 1.8 g (53%)

m.p.=172–174° C. (hexane/ethyl acetate)

Elemental analysis: $C_{16}H_{18}N_2O_7S_2$ (M=414.44)

|  | C % | H % | N % | S % |
|---|---|---|---|---|
| calculated | 46.37 | 4.38 | 6.76 | 15.47 |
| found | 46.34 | 4.29 | 6.74 | 15.29 |

IR: $\bar{\nu}$=3261, 1595, 1559, 1486, 1335, 1323, 1282, 1166, 157, 1132, 1072, 600 cm$^{-1}$ $^1$H NMR (DMSO d$_6$): δ=2.59 (6H, (3H, s); 6.57 (2H, s, exchangeable with CF$_3$COOD); 7.10 (2H, s); 7.23–7.29 (1H, m); 7.34 (1H, d, J=8.1 Hz); 7.74–7.80 (1H, m); 8.06–8.09 (1H, m); 10.99 (1H, s, exchangeable with CF$_3$COOD).

EXAMPLE 45

(Method A2) N-[3,5-Dimethyl-4-[(nitromethyl)sulphonyl]phenyl]-2-methylbenzenesulphonamide The title compound is obtained by working as in Example 27, starting with a solution of 2.6 g (10.6 mmol) of 3,5-dimethyl-4-[(nitromethyl)sulphonyl]aniline in 65 ml of tetrahydrofuran, 1.69 ml (20.9 mmol) of pyridine and 3 g (15.7 mmol) of ortho-toluenesulphonyl chloride.

The mixture is stirred at room temperature for 24 hours, then heated at 40° C. for 8 hours and then left for 24 hours at room temperature.

Yield: 0.29 g (6.8%)

m.p.=118–120° C. (hexane/ethyl acetate)

Elemental analysis: $C_{16}H_{18}N_2O_6S_2$ (M=398.44)

|  | C% | H% | N% | S% |
|---|---|---|---|---|
| calculated | 48.23 | 4.55 | 7.03 | 16.09 |
| found | 48.37 | 4.40 | 7.10 | 15.77 |

The NMR indicates the presence of the ortho-methyl isomer (about 50%) mixed with the meta- and paraisomers (about 50% for the two) arising from the fact that the commercial ortho-toluenesulphonyl chloride (TCI) is in fact a mixture of isomers (as indicated by its NMR spectrum).

EXAMPLE 46

(Method A2)

N-[3,5-Dimethyl-4-[(nitromethyl)sulphonyl]phenyl]-3-methoxybenzenesulphonamide

The title compound is obtained by working as in Example 2, starting with 2 g (8.18 mmol) of 3,5-dimethyl-4-[(nitromethyl)sulphonyl]aniline, 50 ml of tetrahydrofuran, 1.3 ml (16.1 mmol) of pyridine and 2.5 g (12.3 mmol) of 3-methoxybenzenesulphonyl chloride (prepared according to M. Ludwig et al., Collect. Czech. Chem. Commun. 1984, 49, (5), 1182).

Yield: 0.83 g (24.7%)

m.p.=166–168° C. (hexane/ethyl acetate)

Elemental analysis: $C_{16}H_{18}N_2O_7S_2$ (M=414.44)

|  | C% | H% | N% | S% |
|---|---|---|---|---|
| calculated | 46.37 | 4.38 | 6.76 | 15.47 |
| found | 46.37 | 4.48 | 6.70 | 15.31 |

$^1$H NMR (DMSO d$_6$): δ=3.85 (3H, s); 6.5 (2H, s, exchangeable with CF$_3$COOD); 7.05 (2H, s); 7.25 to 7.65 (4H, m); 11.1 (1H, s, exchangeable with CF$_3$COOD).

EXAMPLE 47

(Method A1)

N-[3,5-Dimethyl-4-[(nitromethyl)sulphonyl]phenyl]-3-pyridinesulphonamide

The title compound is obtained by working as in Example 5, starting with 1.7 g (7 mmol) of 3,5-dimethyl-4-[(nitromethyl)sulphonyl]aniline, 40 ml of tetrahydrofuran, 2.8 g (28 mmol) of CaCO$_3$ and 1.9 g (10.5 mmol) of 3-pyridinesulphonyl chloride (prepared according to Fuerst et al., J. Prakt. Chem., 1967, 36, 160), stirring for 5 hours at room temperature.

The crude product is chromatographed on silica with a CH$_2$Cl$_2$/MeOH (98:2) mixture and then recrystallized from a hexane/ethyl acetate mixture.

Yield: 0.11 g (4%)

m.p.=191–192° C. (hexane/ethyl acetate)

Elemental analysis: $C_{14}H_{15}N_3O_6S_2$ (M=385.42)

|  | C% | H% | N% | S% |
|---|---|---|---|---|
| calculated | 43.63 | 3.92 | 10.90 | 16.64 |
| found | 43.62 | 3.99 | 10.91 | 16.76 |

$^1$H NMR (DMSO d$_6$): δ=6.5 (2H, s, exchangeable with CF$_3$COOD); 7.03 (2H, s); 7.64 (1H, dd); 8.28 (1H, dt); 8.85 (1H, dd); 9.06 (1H, d); 11.3 (1H, s, exchangeable with CF$_3$COOD).

EXAMPLE 48

(Method A2)

N-[3,5-Dimethyl-4-[(nitromethyl)sulphonyl]phenyl]-(2-trifluoromethylphenyl)methanesulphonamide The title compound is obtained by working as in Example 2, starting with 3 g (12.28 mmol) of 3,5-dimethyl-4-[(nitromethyl)sulphonyl]aniline, 57 ml of anhydrous tetrahydrofuran, 2 ml (24.7 mmol) of pyridine and 4.8 g (18.5 mmol) of (2-trifluoromethylphenyl)methanesulphonyl chloride (prepared according to Hamer et al., J. Pharm. Sci., 1975, 64, 1961). The product obtained is recrystallized from a hexane/ethyl acetate mixture.

Yield: 1.37 g (24%)

m.p. 146–148° C. (hexane/ethyl acetate)

Elemental analysis: $C_{17}H_{17}F_3N_2O_6S_2$

|  | C% | H% | F% | N% | S% |
|---|---|---|---|---|---|
| calculated | 43.77 | 3.67 | 12.22 | 6.01 | 13.75 |
| found | 43.72 | 3.90 | 11.97 | 6.03 | 13.65 |

$^1$H NMR (DMSO $d_6$): δ=2.3 (6H, s); 4.6 (2H, s); 6.27 (2H, s, exchangeable with $CF_3COOD$); 6.71 (2H, s); 7.4 to 7.6 (4H, m); 10.6 (1H, s, exchangeable with $CF_3COOD$)

EXAMPLE 49

(Method A2)

N-[3,5-Dimethyl-4-[(nitromethyl)sulphonyl]phenyl]-(3-fluorophenyl)methanesulphonamide The title compound is obtained by working as in Example 2, starting with 3 g (12.28 mmol) of 3,5-dimethyl-4-[(nitromethyl)sulphonyl]aniline, 57 ml of anhydrous tetrahydrofuran, 2 ml (24.7 mmol) of pyridine and 3.85 g (18.4 mmol) of (3-fluorophenyl)methanesulphonyl chloride (prepared according to U.S. Pat. No. 3,471,474). The product is recrystallized from a hexane/ethyl acetate mixture.

Yield: 0.45 g (8.8%)

m.p.=172–174° C. (hexane/EtOAc)

Elemental analysis: $C_{17}H_{17}FN_2O_6S_2$ (M=416.45)

|  | C% | H% | F% | N% | S% |
|---|---|---|---|---|---|
| calculated | 46.15 | 4.11 | 4.56 | 6.73 | 15.40 |
| found | 45.96 | 4.05 | 4.62 | 6.73 | 15.44 |

$^1$H NMR (DMSO $d_6$): δ=2.28 (6H, s); 4.5 (2H, s); 6.24 (2H, s, exchangeable with $CF_3COOD$); 6.71 (2H, s); 6.85 to 7.0 (3H, m); 7.11 to 7.21 (1H, m); 10.25 (1H, s, exchangeable with $CF_3COOD$)

EXAMPLE 50

(Method A2)

N-[3 [[3, 5-Dimethyl-4-[(nitromethyl)sulphonyl] phenylamino]sulphonyl]phenyl]acetamide The title compound is obtained by working as in Example 2, starting with 2 g (8.18 mmol) of 3,5-dimethyl-4-[(nitromethyl)sulphonyl]aniline, 50 ml of anhydrous tetrahydrofuran, 1.3 ml (16.1 mmol) of pyridine and a solution of 3.8 g (16.2 mmol) of 3-acetylaminobenzenesulohonyl chloride (prepared according to Barco et al., Synthesis, 1974, 877) in 50 ml of anhydrous tetrahydrofuran. After evaporation of the extraction solvent, the residue is chromatographed on silica with a mixture of hexane and ethyl acetate (1:1) as eluent, and then recrystallized twice from methylene chloride.

Yield: 0.775 g (21.4%)

m.p.=108–110° C. ($CH_2Cl_2$)

Elemental analysis: $C_{17}H_{19}N_3O_7S_2$ (M=441.48)

|  | C% | H% | N% | S% |
|---|---|---|---|---|
| calculated | 46.25 | 4.34 | 9.52 | 14.53 |
| found | 46.15 | 4.5 | 9.29 | 14.17 |

$^1$H NMR (DMSO $d_6$): δ=2.08 (3H, s); 2.48 (6H, s); 6.45 (2H, s, exchangeable with $CF_3COOD$); 7.0 (2H, s); 7.5 to 7.7 (3H, m); 8.36 (1H, s); 10.3 (1H, s, exchangeable with $CF_3COOD$); 11.15 (1H, s exchangeable with $CF_3COOD$)

EXAMPLE 51

(Method A2)

N-[3,5-Dimethyl-4-[(nitromethyl)sulphonyl]phenyl]-(2-methylphenyl)methanesulphonamide The title compound is obtained by working as in Example 2, starting with 2 g (8.18 mmol) of 3,5-dimethyl-4-[(nitromethyl)sulphonyl]aniline, 38 ml of anhydrous tetrahydrofuran, 1.3 ml (16.1 mmol) of pyridine and 2.5 g (12.2 mmol) of (2-methylphenyl)methanesulphonyl chloride.

After evaporation of the extraction solvent, the residue is chromatographed on silica, a first time using methylene chloride as eluent, and then a second time using a hexane/ethyl acetate mixture (1:1).

Finally, the product is recrystallized from a hexane/ethyl acetate mixture.

Yield: 0.19 g (5.6%)

m.p.=167–169° C. (hexane/EtOAc)

Elemental analysis; $C_{17}H_{20}N_2O_6S_2$ (M=412.49)

|  | C% | H% | N% |
|---|---|---|---|
| calculated | 49.50 | 4.89 | 6.79 |
| found | 49.73 | 4.90 | 6.55 |

$^1$H NMR (DMSO $d_6$): δ=2.3 (3H, s); 2.5 (6H, s); 4.68 (2H, s); 6.43 (2H, s, exchangeable with $CF_3COOD$); 6.91 (2H, s); 7.1 to 7.3 (4H, m); 10.5 (1H, s, exchangeable with $CF_3COOD$)

The starting material, (2-methylphenyl)methanesulphonyl chloride is prepared from alpha-chloro-ortho-xylene according to the process of J. Nakayama et al., Tetrahedron Letters, 1984, 25 (40) 4553.

Yield: 31% m.p.=46–48° C.

$^1$H NMR ($CDCl_3$): δ=2.4 (3H, s); 4.9 (2H, s); 7.15 to 7.40 (4H, m)

EXAMPLE 52

(Method A2)

4-Bromo-N-[3,5-dimethyl-4-[(nitromethyl) sulphonyl]phenyl]-(2-fluorophenyl) methanesulphonamide The title compound is obtained by working as in Example 2, starting with 3 g (12.28 mmol) of 3,5-dimethyl-4-

[(nitromethyl)sulphonyl]aniline, 57 ml of anhydrous tetrahydrofuran, 2 ml (24.7 mmol) of pyridine and 5.3 g (19.78 mmol) of (4-bromo-2-fluorophenyl)methanesulphonyl chloride. After evaporation of the solvent, the residue is chromatographed twice on silica, eluting with $CH_2Cl_2$, and recrystallized twice from a hexane/ethyl acetate mixture.

Yield: 1.1 g (18%)

m.p.=152–154° C. (hexane/EtOAc)

Elemental analysis: $C_{16}H_{16}BrFN_2O_6S_2$ (M=495.35)

| | C% | H% | Br% | F% | N% | S% |
|---|---|---|---|---|---|---|
| calculated | 38.80 | 3.26 | 16.13 | 3.84 | 5.66 | 12.95 |
| found | 38.64 | 3.22 | 16.15 | 3.30 | 5.50 | 12.86 |

$^1$H NMR (DMSO $d_6$); δ=2.65 (6H, s); 4.85 (2H, s) 6.60 (2H, s, exchangeable with $CF_3COOD$); 7.08 (2H, s); 7.45 to 7.74 (3H, m); 10.8 (1H, s, exchangeable with $CF_3COOD$)

The starting material, (4-bromo-2-fluorophenyl)methanesulphonyl chloride is prepared from 4-bromo-2-fluorobenzyl bromide according to the process of J. Nakayama et al., Tetrahedron Letters, 1984, 25 (40), 4553.

Yield: 90%

Oil purified by flash chromatography on $SiO_2$, eluting with $CH_2Cl_2$.

$^1$H NMR ($CDCl_3$): δ=4.8 (2H, s); 7.2 to 7.4 (4H, m)

EXAMPLE 53

(Method A2)

N-[3,5-Dimethyl-4-[(nitromethyl)sulphonyl]phenyl]cyclohexylmethanesulphonamide 3.2 g (16.1 mmol) of cyclohexylmethanesulphonyl chloride (prepared according to J. F. King et al., J. Am. Chem. Soc., 1992, 114 (5), 1743) are added dropwise to a mixture, cooled to −20° C. and under a nitrogen atmosphere, of 2 g (8.18 mmol) of 3,5-dimethyl-4-[(nitromethyl)sulphonyl]aniline, 50 ml of anhydrous tetrahydrofuran and 1.3 ml (16.1 mmol) of pyridine, and the resulting mixture is stirred for 6 hours at −20° C. The mixture is left overnight at −20° C., it is then allowed to warm to room temperature and is stirred for 24 hours at room temperature and then refluxed for 13 hours. The mixture is cooled, poured into water, acidified to pH=3 with 1N HCl, extracted with $CH_2Cl_2$, washed with water, dried over $Na_2SO_4$, filtered and evaporated under vacuum. The residue is purified by chromatography on silica, eluting with $CH_2Cl_2$, and then recrystallized from a hexane/ethyl acetate mixture.

Yield: 0.085 g (2.5%)

m.p.=126–128° C.

Elemental analysis: $C_{16}H_{24}N_2O_6S_2$+17% $C_6H_{14}$ (M=404.51+0.17×86.18)

| | C% | H% | N% | S% |
|---|---|---|---|---|
| calculated | 48.77 | 6.34 | 6.68 | 15.30 |
| found | 48.53 | 6.20 | 6.66 | 14.91 |

$^1$H NMR (DMSO $d_6$): δ=1.0 to 1.3 (5H, m); 1.5 to 1.7 (3H, m); 1.75 to 1.90 (3H, m); 2.5 (6H, s); 3.15 to 3.22 (2H, m); 6.48 (2H, s, exchangeable with $CF_3COOD$); 7.03 (2H, s); 10.5 (1H, s, exchangeable with $CF_3COOD$)

EXAMPLE 54

Sodium Salt of N-[3,5-dimethyl-4-[(nitromethyl)sulphonyl]phenyl]benzenesulphonamide A mixture of 0.34 g (0.884 mmol) of N-[3,5-dimethyl-4-[(nitromethyl)sulphonyl]phenyl]benzenesulphonamide and 0.149 g (1.77 mmol) of sodium bicarbonate in 15 ml of distilled water is stirred for 24 hours at room temperature.

The solution obtained is evaporated under high vacuum at a temperature ≦30° C. The solid residue is washed with ether, dried under vacuum and recrystallized from a methanol/ether mixture.

Yield: 0.22 g (58%)

m.p.=253–255° C. (MeOH/$Et_2O$)

Elemental analysis: $C_{15}H_{14}N_2Na_2O_6S_2$+0.65 $H_2O$ (M=440.11)

| | C% | H% | N% | Na% | S% |
|---|---|---|---|---|---|
| calculated | 40.94 | 3.50 | 6.37 | 10.45 | 14.57 |
| found | 41.18 | 3.43 | 6.46 | 10.52 | 14.25 |

$^1$H NMR (DMSO $d_6$): δ=2.44 (6H, s); 6.98 (2H, s); 7.05 (1H, s, exchangeable with $CF_3COOD$); 7.46 to 7.65 (3H, m); 7.8 to 7.9 (2H, m)

EXAMPLE 55

Calcium Salt of N-[3,5-dimethyl-4-[(nitromethyl)sulphonyl]phenyl]benzenesulphonamide A mixture of 0.34 g (0.88 mmol) of N-[3,5-dimethyl-4-[(nitromethyl)sulphonyl]phenyl]benzenesulphonamide and 0.033 g (0.88 mmol) of calcium hydroxide in 20 ml of deionized water is stirred for 1 hour at 25° C. and then for 15 min at 70° C. The solution obtained is filtered while hot and evaporated under vacuum. The residual solid is recrystallized from a methanol/ether mixture.

Yield: 0.08 g (22%)

m.p.=195–197° C. (MeOH/$Et_2O$)

Elemental analysis: $C_{30}H_{30}CaN_4O_{12}S_4$+2$H_2O$ (M=842.93)

| | C% | H% | Ca% | N% | S% |
|---|---|---|---|---|---|
| calculated | 42.75 | 4.06 | 4.75 | 6.65 | 15.21 |
| found | 42.52 | 4.17 | 4.74 | 6.40 | 14.81 |

$^1$H NMR (DMSO $d_6$): δ=2.43 (6H, s); 6.5 (1H, s, exchangeable with $CF_3COOD$); 6.7 (2H, s); 7.4 to 7.6 (3H, m); 7.7 to 7.8 (2H, m); 10.5 (1H, s, exchangeable with $CF_3COOD$)

EXAMPLE 56

(Method F1)

N,N'-Bis[3,5-dimethyl-4-[(nitromethyl)sulphonyl]phenyl]-1,8-octanediamide 0.8637 g (4.09 mmol) of suberoyl chloride is added to a mixture of 2 g (8.18 mmol) of 3,5-dimethyl-4-[(nitromethyl)

sulphonyl]aniline, 50 ml of anhydrous tetrahydrofuran and 1.64 g (16.3 mmol) of calcium carbonate, maintained under a nitrogen atmosphere, and the resulting mixture is stirred overnight at room temperature. This mixture is poured into water, acidified to pH=3 with dilute HCl and the insoluble material is filtered off. The filtrate is extracted with ethyl acetate and the organic phase is washed with water, dried over sodium sulphate, filtered and evaporated under vacuum. The residue obtained is combined with the first insoluble material and recrystallized from an ethanol/DMF mixture.

Yield: 0.79 g (15.4%)

m.p.=235–238° C. (EtOH/DMF)

Elemental analysis: $C_{26}H_{34}N_4O_{10}S_2$ (M=626.68)

|  | C% | H% | N% | S% |
|---|---|---|---|---|
| calculated | 49.83 | 5.47 | 8.94 | 10.23 |
| found | 49.96 | 5.60 | 9.16 | 9.86 |

IR: $\bar{v}$=3363 and 1667 cm$^{-1}$ $^1$H NMR (DMSO d$_6$): δ=1.25 to 1.35 (4H, m); 1.5 to 1.6 (4H, m); 2.3 (4H, t); 2.48 (12H, s); 6.42 (4H, s, exchangeable with CF$_3$COOD); 7.5 (4H, s); 10.2 (2H, s, exchangeable with CF$_3$COOD)

EXAMPLE 57

(Method F1)

N,N'-Bis[3,5-dimethyl-4-[(nitromethyl)sulphonyl]phenyl]-1,5-pentanediamide 0.691 g (4.09 mmol) of glutaryl dichloride is added to a mixture of 2 g (8.18 mmol) of 3,5-dimethyl-4-[(nitromethyl)sulphonyl]aniline, 50 ml of anhydrous tetrahydrofuran and 1.64 g (16.3 mmol) of calcium carbonate, maintained under a nitrogen atmosphere, and the resulting mixture is stirred for 24 hours at room temperature. This mixture is poured into water, acidified to pH=3 with dilute HCl, extracted with ethyl acetate and washed with water, and the organic phase is dried over Na$_2$SO$_4$, filtered and evaporated under vacuum. The solid obtained is recrystallized from a hexane/ethyl acetate mixture.

Yield: 0.49 g (20%)

m.p.=207–210° C. (hexane/EtOAc)

Elemental analysis: $C_{23}H_{28}N_4O_{10}S_2$ (M=584.606)

|  | C% | H% | N% | S% |
|---|---|---|---|---|
| calculated | 47.25 | 4.83 | 9.58 | 10.97 |
| found | 47.06 | 4.87 | 9.46 | 10.65 |

IR: $\bar{v}$=3300 and 1684 cm$^1$ $^1$H NMR (DMSO d$_6$): δ=1.63 (2H, q); 2.18 (4H, t) ; 2.28 (12H, s); 6.22 (4H, s, exchangeable with CF$_3$COOD); 7.3 (4H, s); 10.04 (2H, s, exchangeable with CF$_3$COOD)

EXAMPLE 58

(Method G1)

N,N'-Bis[3,5-dimethyl-4-[(nitromethyl)sulphonyl]phenyl]-1,3-benzenedisulphonamide 1.1 g (4.09 mmol) of 1,3-benzenedisulphonyl chloride are added in a single portion to a mixture of 2 g (8.18 mmol) of 3,5-dimethyl-4-[(nitromethyl)sulphonyl]aniline, 38 ml of anhydrous tetrahydrofuran and 1.63 g (16.1 mmol) of calcium carbonate, maintained under a nitrogen atmosphere. The mixture is stirred for 24 hours at room temperature and then for 40 hours at 50° C.

This mixture is cooled to room temperature, poured into water, extracted with CH$_2$Cl$_2$, washed with water, dried over Na$_2$SO$_4$, filtered and evaporated under vacuum. The residue is purified by chromatography on silica (at a temperature of −30° C.), eluting first with CH$_2$Cl$_2$ in order to remove the starting material, and then with a CH$_2$Cl$_2$/EtOAc mixture (3:1), in order to obtain the expected product, which is recrystallized a first time from a hexane/CH$_2$Cl$_2$ mixture, and then a second time from an EtOAc/hexane/CH$_2$Cl$_2$ mixture.

Yield: 0.4 g (14%)

m.p.=191–192° C. (EtOAc/hexane/CH$_2$Cl$_2$)

Elemental analysis: $C_{24}H_{26}N_4O_{12}S_4$+0.18 CH$_3$COOEt (M=706.62)

|  | C% | H% | N% | S% |
|---|---|---|---|---|
| calculated | 42.02 | 3.91 | 7.93 | 18.15 |
| found | 42.22 | 3.99 | 7.96 | 17.75 |

IR: $\bar{v}$=3245, 1595 and 1559 cm$^{-1}$ $^1$H NMR (DMSO d$_6$): δ=2.54 (12H, s); 6.51 (4H, s, exchangeable with CF$_3$COOD); 7.06 (4H, s); 7.9 (1H, t); 8.2 (2H, d); 8.48 (1H, s); 11.4 (2H, s, exchangeable with CF$_3$COOD)

EXAMPLE 59

(Method F1)

N,N'-Bis[3,5-dimethyl-4-[(nitromethyl)sulphonyl]phenyl]ethanediamide 0.35 ml (4.09 mmol) of oxalyl chloride is added to a mixture of 2 g (8.18 mmol) of 3,5-dimethyl-4-[(nitromethyl)sulphonyl]aniline, 50 ml of anhydrous tetrahydrofuran and 1.63 g (16.2 mmol) of calcium carbonate, maintained under a nitrogen atmosphere. The mixture is stirred for 3 days at room temperature and poured into water. The precipitate obtained is filtered off, washed with water, dried under vacuum and recrystallized from an ethanol/dimethylformamide mixture.

Yield: 1.62 g (73%)

m.p.=246–248° C. (EtOH/DMF)

Elemental analysis: $C_{20}H_{22}N_4O_{10}S_2$ (M=542.528)

|  | C% | H% | N% | S% |
|---|---|---|---|---|
| calculated | 44.27 | 4.09 | 10.33 | 11.82 |
| found | 44.35 | 4.23 | 10.34 | 11.62 |

IR: $\bar{v}$=3340 and 1700 cm$^{-1}$ $^1$H NMR (DMSO d$_6$): δ=2.58 (12H, s); 6.56 (4H, s, exchangeable with CF$_3$COOD); 7.84 (4H, s); 11.2 (2H, s, exchangeable with CF$_3$COOD)

EXAMPLE 60

(Method F1)

N,N'-Bis[4-[(nitromethyl)sulphonyl]phenyl]-1,5-pentane diamide 0.78 g (4.63 mmol) of glutaryl dichloride is added to a mixture of 2 g (9.25 mmol) of 4-[(nitromethyl) sulphonyl]

aniline (prepared according to U.S. Pat. No. 5,153,227), 50 ml of anhydrous tetrahydrofuran and 1.85 g (18.5 mmol) of calcium carbonate, maintained under a nitrogen atmosphere. The mixture is stirred for 4 days at room temperature and then heated at 40° C. for 24 hours and at 60° C. for 16 hours. This mixture is cooled, poured into a water+ice mixture and stirred for 4 hours at 0° C. The precipitate obtained is filtered off, washed with water and dissolved in ethyl acetate. The organic phase is washed with water, dried over $Na_2SO_4$, filtered and evaporated under vacuum. The solid obtained is recrystallized from ethanol.

Yield: 0.88 g (37%)

m.p.=203–205° C. (EtOH)

Elemental analysis: $C_{19}H_{20}N_4O_{10}S_2$ (M=528.52)

|  | C% | H% | N% | S% |
|---|---|---|---|---|
| calculated | 43.18 | 3.81 | 10.60 | 12.13 |
| found | 43.20 | 3.94 | 10.42 | 11.92 |

$^1$H NMR (DMSO $d_6$): δ=1.9 to 2.1 (2H, m); 2.55 (4H, t); 6.6 (4H, s, exchangeable with $CF_3COOD$); 7.95 (8H, s); 10.56 (2H, s, exchangeable with $CF_3COOD$)

EXAMPLE 61

(Method F1)

N,N-Bis[3,5-dimethyl-4-[(nitromethyl)sulphonyl] phenyl]1,4-butanediamide 0.64 g (4.14 mmol) of succinyl chloride is added to a mixture of 2 g (8.18 mmol) of 3,5-dimethyl 4[(nitromethyl) sulphonyl]aniline, 50 ml of anhydrous tetrahydrofuran and 1.6 g (16.3 mmol) of calcium carbonate, maintained under a nitrogen atmosphere, and the mixture is stirred for 6 days at room temperature. This mixture is poured into an ice+water mixture, acidified to pH=3 with 1N HCl and the precipitate obtained is filtered off, washed with water and dried under vacuum. The solid obtained is washed with hot ethyl acetate and then recrystallized from ethanol.

Yield: 0.115 g (4.8%)

m.p.=226–228° C. (EtOH)

Elemental analysis: $C_{22}H_{26}N_4O_{10}S_2$+0.06 EtOH+0.5 $H_2O$ (M=580.199)

|  | C% | H% | N% | S% |
|---|---|---|---|---|
| calculated | 45.63 | 4.74 | 9.62 | 11.01 |
| found | 46.03 | 4.63 | 9.63 | 10.53 |

$^1$H NMR (DMSO $d_6$): δ=2.5 (6H, s); 2.7 (4H, s); 6.44 (4H, s, exchangeable with $CF_3COOD$); 7.5 (4H, s); 10.4 (2H, s, exchangeable with $CF_3COOD$)

EXAMPLE 62

(Method F1)

N,N'-Bis[3,5-dimethyl-4-[(nitromethyl)sulphonyl] phenyl]-1,3-propanediamide 0.58 g (4.14 mmol) of malonyl dichloride is added to a mixture of 2 g (8.18 mmol) of 3,5-dimethyl-4-[(nitromethyl) sulphonyl]aniline, 50 ml of anhydrous tetrahydrofuran and 1.6 g (16.3 mmol) of calcium carbonate, maintained under a nitrogen atmosphere, and the mixture is stirred for 24 hours at room temperature. This mixture is poured onto an ice+water mixture, acidified to pH=3 with 1N HCl, extracted with ethyl acetate, washed with water, dried over $Na_2SO_4$, filtered and evaporated under vacuum. The solid obtained is recrystallized from a hexane/ethyl acetate mixture.

Yield: 0.2 g (9.8%)

m.p.=197–199° C. (hexane/EtOAc)

Elemental analysis: $C_{21}H_{24}N_4O_{10}S_2$+0.5 $H_2O$+0.1 EtOAc (M=574.396)

|  | C% | H% | N% | S% |
|---|---|---|---|---|
| calculated | 44.75 | 4.53 | 9.75 | 11.17 |
| found | 44.88 | 4.56 | 9.62 | 10.78 |

$^1$H NMR (DMSO$d_6$): δ=2.6 (12H, s); 3.65 (2H, s); 6.55 (4H, s, exchangeable with $CF_3COOD$); 7.6 (4H, s); 10.6 (2H, s, exchangeable with $CF_3COOD$)

EXAMPLE 63

(Method H)

N,N'-Bis[3,5-dimethyl-4-[(nitromethyl)sulphonyl] phenyl]urea 0.5 ml (4.09 mmol) of trichloromethyl chloroformate is added dropwise to a mixture of 2 g (8.18 mmol) of 3,5-dimethyl-4-[(nitromethyl)sulphonyl]aniline, 60 ml of anhydrous tetrahydrofuran and 0.54 g (5.39 mmol) of calcium carbonate, maintained under nitrogen atmosphere. The mixture is stirred for 24 hours at room temperature, refluxed for 8 hours and left for 4 days at room temperature. This mixture is poured into water and the precipitate obtained is filtered off, dried and recrystallized from ethanol.

Yield: 0.48 g (20%)

m.p.=224–226° C. (EtOH)

Elemental analysis: $C_{19}H_{22}N_4O_9S_2$+0.3 EtOH+0.3 $H_2O$ (M=533.765)

|  | C% | H% | N% | S% |
|---|---|---|---|---|
| calculated | 44.11 | 4.61 | 10.50 | 12.02 |
| found | 44.43 | 4.43 | 10.75 | 11.76 |

$^1$H NMR (DMSO $d_6$): δ=2.53 (12H, s); 6.49 (4H, s, exchangeable with $CF_3COOD$); 7.4 (4H, s); 9.33 (2H, s, exchangeable with $CF_3COOD$)

EXAMPLE 64

(Method G2)

N,N'-Bis[3,5-dimethyl-4-[(nitromethyl)sulphonyl] phenyl]-1,3-benzenedimethanesulphonamide 2.5 g (8.2 mmol) of 1,3-benzenedimethanesulphonyl dichloride (prepared according to J. Lichtenberger et al., Bull. Soc. Chim. Fr. 1961, 369) are added in a single portion to a mixture of 4 g (16.3 mmol) of 3,5-dimethyl-4-[(nitromethyl)sulphonyl]aniline, 76 ml of anhydrous tetrahydrofuran and 5.2 ml (64.3 mmol) of pyridine, maintained under a nitrogen atmosphere, and the mixture is stirred overnight at room temperature. This mixture is poured into 500 ml of water, acidified with 1N HCl, extracted with $CH_2Cl_2$, washed with water, dried over $Na_2SO_4$, filtered and evaporated under vacuum. The residue is purified by chromatography on silica, eluting with $CH_2Cl_2$, and then recrystallized from a $CH_2Cl_2$/hexane mixture and chromatographed again on silica, eluting with an EtOAc/hexane mixture (1:1).

Yield: 0.35 g (6%)

m.p.=124–130° C. (EtOAc/hexane)

Elemental analysis: $C_{26}H_{30}N_4O_{12}S_4$+0.3 EtOAc+0.2 $H_2O$ (M=748.847)

|  | C% | H% | N% | S% |
|---|---|---|---|---|
| calculated | 43.63 | 4.41 | 7.48 | 17.13 |
| found | 43.96 | 4.44 | 7.27 | 17.05 |

$^1H$ NMR (DMSO $d_6$); δ=2.5 (12H, s); 4.6 (4H, s); 6.48 (4H, exchangeable with $CF_3COOD$); 6.95 (4H, s); 7.2 to 7.4 (4H, m); 10.5 (2H, s, exchangeable with $CF_3COOD$).

What is claimed is:

1. A compound of the formula 1

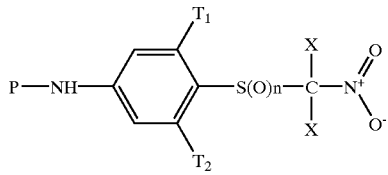

in which

P represents the radical (i): —(CO—NH)$_m$SO$_2$—R; or the radical (iii):

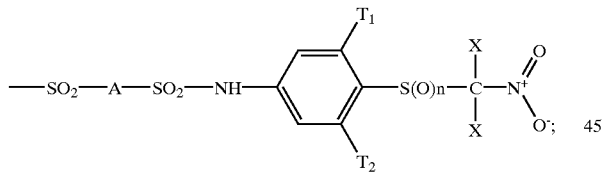

R represents phenyl, benzyl, diphenylmethyl, naphthyl, cycloalkylalkyl in which the alkyl part is $C_1$–$C_4$ and the cycloalkyl part is $C_3$–$C_7$, or styryl, each of which is optionally substituted with one or more groups Z which may be identical or different; or R represents a $C_3$–$C_5$ aromatic heterocyclic radical comprising 1 or 2 hetero atoms O, S or N, said radical optionally being substituted with one or more groups Z, which may be identical or different, and optionally being fused to 1 or 2 phenyl rings which are optionally substituted with one or more groups Z, which may be identical or different; or R represents $C_1$–$C_4$ alkyl optionally substituted with one more halogen atoms, which may be identical or different, $C_3$–$C_7$ cycloalkyl, or cyclo ($C_3$–$C_7$) alkyl ($C_1$–$C_4$) alkyl;

Z is halogen, $C_1$–$C_4$ alkyl, $C_1$–$C_4$ alkoxy, nitro, cyano, trifluoromethyl, trifluoromethoxy, ($C_2$–$C_5$) alkylamino, ($C_1$–$C_4$) alkylsulphonyl, ($C_1$–$C_4$) alkylthio or phenyl;

X represents a hydrogen or halogen atom;

m is 0;

n is 0, 1 or 2;

$T_1$ and $T_2$ represent, independently of each other, a hydrogen atom or a $C_1$–$C_4$ alkyl group, u is 0 or 1;

A represents $C_1$–$C_8$ alkylene or the group

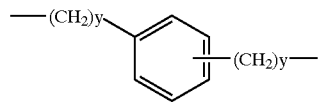

Y is an integer 0, 1, 2, 3 or 4;

A tautomeric form thereof or an addition salt thereof with a pharmaceutically acceptable base.

2. A compound according to claim 1, wherein

P represents —(CO—NH)$_m$—SO$_2$—R; and

R represents phenyl, diphenylmethyl, napthyl or styryl, each of which is optionally substituted with one or more groups Z, which may be identical or different; or R represents a $C_3$–$C_5$ aromatic heterocyclic radical comprising 1 or 2 hetero atoms O, S or N, said radical optionally being substituted with one or more groups Z, which may be identical or different, and optionally being fused to 1 or 2 phenyl rings which are optionally substituted with one or more groups Z, which may be identical or different; or R represents $C_1$–$C_4$ alkyl optionally substituted with one or more halogen atoms, which may be identical or different, $C_3$–$C_7$ cycloalkyl or cyclo ($C_3$–$C_7$) alkyl ($C_1$–$C_4$)-alkyl.

3. A compound according to claim 1, wherein

P represents —(CO—NH)$_m$—SO$_2$—R; and

R represents phenyl; phenyl substituted with one or more groups Z, which may be identical or different; benzyl; benzyl substituted with one or more groups Z which may be identical or different; $C_1$–$C_4$ alkyl optionally substituted with one or more halogen atoms, which maybe identical or different; $C_3$–$C_7$ cycloalkyl; cyclo ($C_3$–$C_7$) alkyl ($C_1$–$C_4$) alkyl; styryl; thienyl; pyridyl; naphthyl; dibenzofuryl; or diphenylmethyl; and Z is halogen, $C_1$–$C_4$ alkyl, $C_1$–$C_4$ alkoxy, nitro, trifluoromethyl, trifluoromethoxy, ($C_2$–$C_5$) alkylamino, ($C_1$–$C_4$) alkylsulphonyl or phenyl.

4. A compound according to claim 1, wherein

P represents —(CO—NH)$_m$—SO$_2$—R;

R represents phenyl; phenyl substituted with one or more groups Z, which may be identical or different; benzyl; benzyl substituted with one or more groups Z which may be identical or different; methyl; $C_3$–$C_7$ cycloalkyl; cyclo ($C_3$–$C_7$) alkyl ($C_1$–$C_4$) alkyl; styryl; thienyl; pyridyl; naphthyl; dibenzofuryl; diphenylmethyl or 2,2,2-trifluoroethyl;

Z is fluoro, chloro, bromo, methyl, methoxy, nitro, trifluoromethyl, trifluoromethoxy, acetamido, methylsulphonyl or phenyl; and X represents hydrogen or chlorine.

5. A compound according to claim 1, wherein

P represents —(CO—NH)$_m$—SO$_2$—R;

R represents phenyl; phenyl substituted with one or more groups Z, which may be identical or different; methyl; $C_3$–$C_7$cycloalkyl; cyclo ($C_3$–$C_7$) alkyl ($C_1$–$C_4$) alkyl;

styryl; thienyl; pyridyl; naphtyl; dibenzofuryl; diphenylmethyl or 2,2,2-trifluoroethyl;

Z is fluoro, chloro, bromo, methyl, methoxy, nitro, trifluoromethyl, trifluoromethoxy, acetamido, methlsulphonyl or phenyl; and X represents hydrogen or chlorine.

6. A compound according to claim 1, wherein said compound is:

N-[3,5-dimethyl-4-[(nitromethyl)sulphonyl]phenyl]-benzenesulphonarnide atautomeric form thereof or an addition salt thereof with a pharmaceutically acceptable base;

3,4-difluoro-N-difluoro-N-[3,5-dimethyl-4-[nitromethyl)sulphonyl]phenyl]benzenesulphonamide a tautomeric form thereof or an addition salt thereof with a pharmaceutically acceptable base;

3-bromo-N-[3,5-dimethyl-4-[(nitromethyl)sulphonyl]-phenyl]benzenesulphonamide a tautomeric form thereof or an addition salt thereof with a pharmaceutically acceptable base;

N-[3,5-dimethyl-4-[(nitromethyl)sulphonyl]phenyl]-2-(trifluoromethyl) benzenesulphonamide a tatutomeric form thereof or an addition salt thereof with a pharmaceutically acceptable base;

N-[3,5-dimethyl-4-[(nitromethyl)sulphonyl]phenyl]-4-fluorobenzenesulphonamide a tautomeric form thereof or an addition salt thereof with a pharmaceutically acceptable base;

N-[3,5-dimethyl-4-[(nitromethyl)sulphonyl]phenyl]-3-fluorobenzenesulphonamide a tautomeric form thereof or an addition salt thereof with a pharmaceutically acceptable base;

N-[3,5-dimethyl-4-[(nitromethyl)sulphonyl]phenyl] phenylmethanesulphonamide a tautomeric form thereof or an addition salt thereof with a pharmaceutically acceptable base;

2,3-difluoro-N-[3,5-dimethyl-4-[(nitromethyl)sulphonyl] phenyl]benzenesulphonamide a tautomeric form thereof or an addition salt thereof with a pharmaceutically acceptable base;

3,5-difluoro-N-[3,5-dimethyl-4-[(nitromethyl)-sulphonyl]phenyl]benzenesulphonamide a tautomeric form thereof or an addition salt thereof with a pharmaceutically acceptable base; or N-[3,5-dimethyl-4-[(nitromethyl)sulphonyl]phenyl]-2-fluorobenzenesulphonamide a tautomeric form thereof or an addition salt thereof with a pharmaceutically acceptable base.

7. Compound of formula 1 according to claim 1, characterized in that:

P represents:

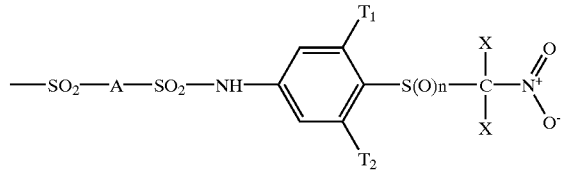

A represents the group

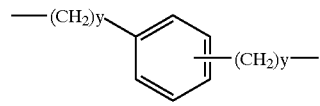

n, X, y, $T_1$ and $T_2$ being as defined in claim 1, the tautomeric forms thereof and the addition salts thereof with pharmaceutically acceptable bases.

8. A compound according to claim 1, chosen from the compounds:

N,N'-bis[3,5-dimethyl-4-[(nitromethyl)sulphonyl]phenyl]-1,5-pentanediamide;

N,N'-bis[3,5-dimethyl-4-[(nitromethyl)sulphonyl]phenyl]-1,8-octanediamide;

N,N'-bis[4-(nitromethyl)sulphonyl]phenyl]-1,5-pentane diamide;

N,N'-bis[3,5-dimethyl-4-[(nitromethyl)sulphonyl]phenyl]-ethanediamide;

N,N'-bis[3,5-dimethyl-4-[(nitromethyl)sulphonyl]phenyl]-1,4-butanediamide;

N,N'-bis[3,5-dimethyl-4-[(nitromethyl)sulphonyl]phenyl]-1,3-propanediamide;

N,N'-bis[3,5-dimethyl-4-[(nitromethyl)sulphonyl]phenyl]-1,3-benzenedisulphonamide;

N,N'-bis[3,5-dimethyl-4-[(nitromethyl)sulphonyl]phenyl]-1,3-benzenedimethane sulphonamide.

9. A process for preparing a compound according to claim 1 in which P represents —(CO—NH)$_m$—SO$_2$—R, X is a hydrogen atom, m is zero and n is equal to 2, comprising treating a compound of formula 2, in which $T_1$ and $T_2$ are as defined in claim 1, with a sulphonyl chloride of formula RSO$_2$Cl in which R is as defined in claim 1, in the presence of a base.

formula 2

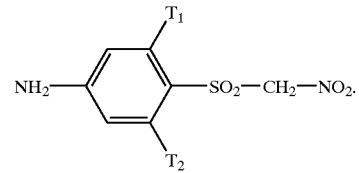

10. A process for preparing a compound according to claim 1 in which P represents (CO—NH)$_m$—SO$_2$—R, X represents a halogen atom, m is zero and n is equal to 2, comprising treating a compound of formula 3 formula 3

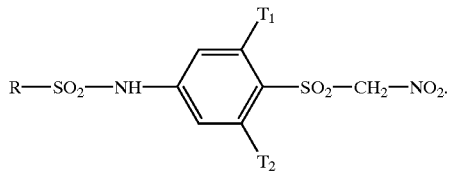

in which R, $T_1$ and $T_2$ are as defined in claim 1, with an N-halosuccinimide in the presence of a free-radical generator.

11. A process for preparing a compound according to claim 1, wherein P represents —(CO—NH)$_m$—SO$_2$—R, X is a hydrogen atom, m is zero and n is equal to 2, comprising treating the compound of formula 2

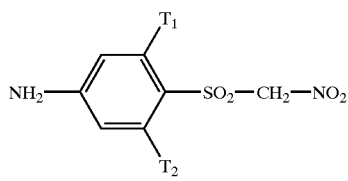

in which $T_1$ and $T_2$ are as defined in claim 1, with a sulphonyl isocyanate of formula $RSO_2NCO$, in which R is as defined in claim 1.

12. A process for preparing a compound according to claim 1, wherein P represents $—(CO—NH)_m—SO_2—R$, X is a hydrogen atom and m and n are equal to zero, comprising treating the compound of formula 10

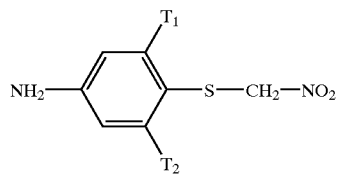

in which $T_1$ and $T_2$ are as defined in claim 1, with a sulphonyl chloride of formula $RSO_2Cl$, in which R is as defined in claim 1, in the presence of a base.

13. A process for preparing a compound according to claim 1, wherein P represents $—(CO—NH)_m—SO_2—R$, X is a hydrogen atom, m is zero and n is equal to 1, comprising treating a compound of formula 4

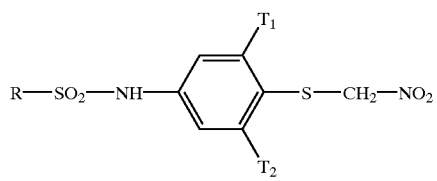

in which R, $T_1$ and $T_2$ are as defined in claim 1, with an oxidizing agent such as m-chlorobenzoic acid.

14. A process for preparing 3,5-dimethyl-4-[(nitromethyl) sulphonyl]aniline by basic hydrolysis comprising reacting nitromethanesodium of formula $NaCH_2NO_2$ with 4-acetamido-2,6-dimethylphenyl thiocyanate.

15. Process for preparing the compounds of formula (1) according to claim 1, in which P represents the radical (iii)

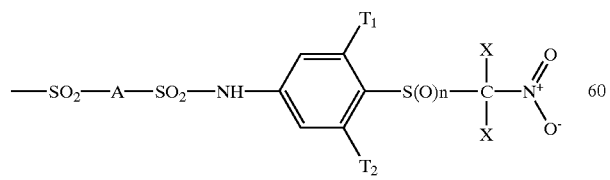

X represents a hydrogen atom and n is equal to 2, characterized in that a compound of formula 2

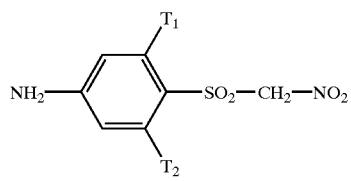

in which $T_1$ and $T_2$ are as defined in claim 1, is treated with a dichloride of formula

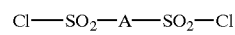

in the presence of a base, the molar ratio of the compound of formula 2 to the compound of formula 6 being at least equal to 2.

16. A pharmaceutical composition comprising an effective amount of at least one compound according to claim 1 in combination with one or more pharmaceutically acceptable vehicles.

17. Pharmaceutical composition according to claim 16, characterized in that it is in the form of immediate-release tablets, controlled-release tablets, gelatin capsules, injectable solutions, creams or eyedrops.

18. A method for inhibiting aldose reductase in a patient comprising administering to said patient an effective amount of a compound of claim 1.

19. A method for treating a diabetic complication in a patient comprising administering to said patient an effective amount of a compound according to claim 1.

20. The method of claim 19, wherein said diabetic complication is a cataract, a retinopathy, a neuropathy, or a vascular disease.

21. A process for preparing a compound of formula 1 formula 1

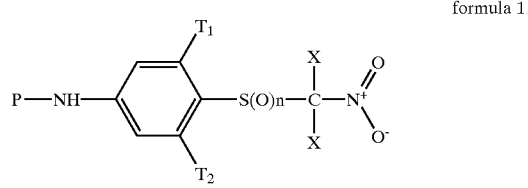

in which

P represents $(CO—NH)_mSO_2—R$, X represents a halogen atom, m is zero and n is equal to 2, comprising treating a compound of formula 3 formula 3

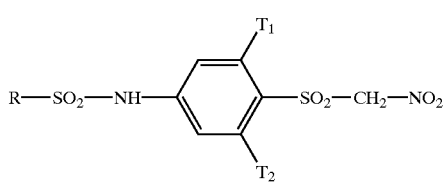

in which

R represents phenyl, benzyl, diphenylmethyl, naphthyl, cycloalkylalkyl in which the alkyl part is $C_1$–$C_4$ and the cycloakyl part is $C_3$–$C_7$, or styryl, each of which is optionally substituted with one or more groups Z which may be identical or different; or R represents a $C_3$–$C_5$ aromatic heterocyclic radical comprising 1 or 2 hetero atoms O, S or N, said radical optionally being substituted with one or more groups Z, which may be identical or different, and optionally being fused to 1 or 2 phenyl rings which are optionally substituted with one or more groups Z, which may be identical or different; or R represents $C_1$–$C_4$ alkyl optionally substituted with one more halogen atoms, which may be identical or different, $C_3$–$C_7$ cycloalkyl, or cyclo ($C_3$–$C_7$) alkyl ($C_1$–$C_4$) alkyl;

Z is halogen, $C_1$–$C_4$ alkyl, $C_1$–$C_4$ alkoxy, nitro, cyano, trifluoromethyl, trifluoromethoxy, ($C_2$–$C_5$) alkylamino, ($C_1$–$C_4$) alkylsulphonyl, ($C_1$–$C_4$) alkylthio or phenyl; and $T_1$ and $T_2$, represent, independently of each other, a hydrogen atom or a $C_1$–$C_4$ alkyl group, with the appropriate N-halosuccinimide in the presence of a free-radical generator a tautomeric form thereof or an addition salt thereof with a pharmaceutically acceptable base.

22. A compound according to claim 1, wherein said compound is:

N,N'-bis[3,5-dimethyl-4-[(nitromethy)sulphonyl]-phenyl]-1,3-benzenedisulphonamide a tautomeric form thereof or an addition salt thereof with a pharmaceutically acceptable base; or N,N'-bis[3,5-dimethyl-4-[(nitromethyl)sulphonyl]-phenyl]-1,3-benzenedimethane sulphonamide a tautomeric form thereof or an addition salt thereof with a pharmaceutically acceptable base.

23. The process according to claim 10, wherein X is chlorine.

24. The process according to claim 21, wherein X is chlorine.

25. A compound of formula 1 formula 1

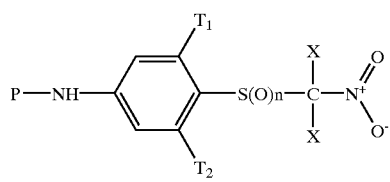

in which

P represents
the radical (i): —(CO—NH)$_m$—SO$_2$—R; or
the radical (iii):

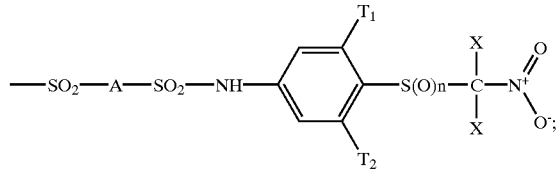

R represents phenyl, benzyl, diphenylmethyl, naphthyl, cycloalkylalkyl in which the alkyl part is $C_1$–$C_4$ and the cycloalkyl part is $C_3$–$C_7$, or styryl, each of which is optionally substituted with one or more groups Z which may be identical or different; or R is selected from furan, thiophene, pyrrole, oxazole, thiazole, imidazole, pyrazole, isoxazole, isothiazole, pyridine, pyridazine, pyrimidine, pyrazine; or R represents $C_1$–$C_4$alkyl optionally substituted with one more halogen atoms, which may be identical or different, $C_3$–$C_7$ cycloalkyl, or cyclo ($C_3$–$C_7$) alkyl ($C_1$–$C_4$) alkyl;

Z is halogen, $C_1$–$C_4$ alkyl, $C_1$–$C_4$ alkoxy, nitro, cyano, trifluoromethyl, trifluoromethoxy, ($C_2$–$C_5$) alkylamino, ($C_1$–$C_4$) alkylsulphonyl, ($C_1$–$C_4$) alkylthio or phenyl;

X represents a hydrogen or halogen atom;

m is 0;

n is 0, 1 or 2;

$T_1$ and $T_2$ represent, independently of each other, a hydrogen atom or a $C_1$–$C_4$ alkyl group, u is 0 or 1;

A represents $C_1$–$C_8$ alkylene or the group

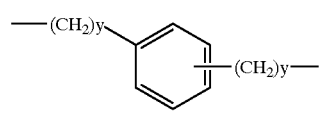

y is an integer 0, 1, 2, 3 or 4;

a tautomeric form thereof or an addition salt thereof with a pharmaceutically acceptable base.

26. The compound of formula I according to claim 1, wherein

P represents

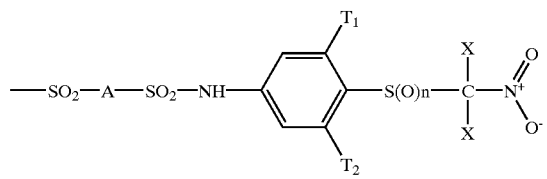

R represents benzyl, diphenylmethyl, naphthyl, cycloalkylalkyl in which the alkyl part is $C_1$–$C_4$ and the cycloalkyl part is $C_3$–$C_7$, or styryl, each of which is optionally substituted with one or more groups Z which may be identical or different; or R represents a $C_3$–$C_5$ aromatic heterocyclic radical comprising 1 or 2 hetero atoms O, S or N, said radical optionally being substituted with one or more groups Z, which may be identical or different, and optionally being fused to 1 or 2 phenyl rings which are optionally substituted with one or more groups Z, which may be identical or different; or R represents $C_3$–$C_7$ cycloalkyl, or cyclo ($C_3$–$C_7$) alkyl ($C_1$–$C_4$) alkyl;

Z is halogen, $C_1$–$C_4$ alkyl, $C_1$–$C_4$ alkoxy, nitro, cyano, trifluoromethyl, trifluoromethoxy, ($C_2$–$C_5$) alkylamino, ($C_1$–$C_4$) alkylsulphonyl, ($C_1$–$C_4$) alkylthio or phenyl;

X represents a hydrogen or halogen atom;

m is 0 or 1;

n is 0, 1 or 2;

$T_1$ and $T_2$ represent, independently of each other, a hydrogen atom or a $C_1$–$C_4$ alkyl group, u is 0 or 1;

A represents

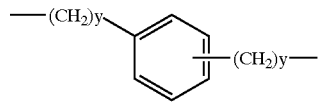

y is an integer 0, 1, 2, 3 or 4;

a tautomeric form thereof or an addition salt thereof with a pharmaceutically acceptable base.

27. The method according to claim 18, wherein the compound of formula I is administered at a daily dosage from 5 mg to 200 mg of active principle.

28. The method according to claim 19, wherein the compound of formula I is administered at a daily dosage from 5 mg to 200 mg of active principle.

* * * * *

UNITED STATES PATENT AND TRADEMARK OFFICE
CERTIFICATE OF CORRECTION

PATENT NO.     : 6,509,499 B1
DATED          : January 21, 2003
INVENTOR(S)    : François Collonges et al.

It is certified that error appears in the above-identified patent and that said Letters Patent is hereby corrected as shown below:

<u>Title page,</u>
Item [75], Inventors, reads "Lyons," should read -- Lyon --

<u>Column 48,</u>
Line 34, reads "-alkyl" should read -- alkyl --
Line 43, reads "maybe" should read -- may be --

<u>Column 49,</u>
Line 4, reads "methlsul-" should read -- methylsul- --
Line 11, reads "benzenesulphonarnide atautomeric" should read
-- benzenesulphoamide, a tautomeric --

<u>Column 50,</u>
Line 18, reads "pentane dia-" should read -- pentanedia- --
Line 48, reads "(CO--NH)$_m$" should read -- -(CO--NH)$_m$ --

<u>Column 52,</u>
Line 67, reads "styryl,each" should read -- styryl, each --

<u>Column 53,</u>
Line 10, reads "one" should read -- one or --
Line 18, reads "T$_2$," should read -- T$_2$ --
Line 27, reads "nitromethy" should read -- nitromethyl --

<u>Column 54,</u>
Line 4, reads "one" should read -- one or --

Signed and Sealed this

Twenty-fifth Day of May, 2004

JON W. DUDAS
*Acting Director of the United States Patent and Trademark Office*